(12) United States Patent
Abdel-Magid et al.

(10) Patent No.: US 7,060,725 B2
(45) Date of Patent: Jun. 13, 2006

(54) SUBSTITUTED SULFAMATE ANTICONVULSANT DERIVATIVES

(75) Inventors: Ahmed Abdel-Magid, Ambler, PA (US); Cynthia Maryanoff, New Hope, PA (US); Steven Mehrman, Lansdale, PA (US); Kirk Sorgi, Doylestown, PA (US); Frank Villani, Perkasie, PA (US); Cheryl Kordik, Lansdale, PA (US); Allen B. Reitz, Lansdale, PA (US); Bruce Maryanoff, New Hope, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 125 days.

(21) Appl. No.: 10/434,387

(22) Filed: May 8, 2003

(65) Prior Publication Data

US 2004/0038911 A1  Feb. 26, 2004

Related U.S. Application Data

(60) Provisional application No. 60/378,017, filed on May 13, 2002.

(51) Int. Cl.
*C07D 323/00* (2006.01)
*A61K 31/335* (2006.01)
(52) U.S. Cl. .............. 514/454; 549/361; 514/321; 514/422; 546/197; 548/526
(58) Field of Classification Search .......... 549/387, 549/396, 426, 427, 336, 337, 433, 443, 361; 514/422, 454, 321; 546/197, 526
See application file for complete search history.

(56) References Cited

U.S. PATENT DOCUMENTS

| | | | |
|---|---|---|---|
| 5,025,031 A | 6/1991 | Lo et al. | |
| 5,192,785 A | 3/1993 | Lo et al. | |
| 5,194,446 A | 3/1993 | Lo et al. | |
| 5,273,993 A | 12/1993 | Lo et al. | |
| 5,952,187 A | 9/1999 | Stenglein et al. | |

FOREIGN PATENT DOCUMENTS

| | | |
|---|---|---|
| EP | 0138441 | 4/1985 |
| EP | 0403185 A2 | 12/1990 |
| EP | 0533483 | 3/1993 |
| WO | WO 95/17406 | 6/1995 |
| WO | WO 97/13510 | 4/1997 |
| WO | WO 97/19950 | 6/1997 |

OTHER PUBLICATIONS

Caldwell, G. et al.: Electron Ionization Mass Spectra of Novel 2,3:4,5-Bis-O-(1-methylethylidene)-β-D-fructopyranose Derivatives and Related Sugar Sulfamates, Org. Mass Spec, 1989, vol. 24, 12 p. 1051-9.

Duan, S. et al.: Photochemical Reactions of Imidazole-1-Sulfonates (Imidazylates), J. Carbohydrate Chemistry, 17(3), 391-396 (1998).

Hanessian, S. et al.: "Design and Reactivity of Organic Functional Groups: Imidazolylsulfonate (Imidazylate)—An Efficient and Versatile Leaving Group", Tetrahedron Letters, vol. 22, No. 37, (1981) pp. 3579-3582.

Kochetkov, N.K. et al., Monosaccharides XXVIII. Synthesis of Monosaccharide Sulfamates from Salts of Monosaccharides Hydrogen Sulfates, Reports of the USSR Academy of Sciences, 1974, vol. 21b, No. 1, pp. 2755-2757.

Kochetkov, N.K. et al., Monosaccharides XXIV. Synthesis of Some Monosaccharide Sulfamates, Reports of the USSR Academy of Sciences, 1974, vol. 21b, No. 1, pp. 1874-1878.

(Continued)

*Primary Examiner*—Zinna Northington Davis
(74) *Attorney, Agent, or Firm*—Mary Appollina

(57) ABSTRACT

The present invention is directed to novel compounds of the formula (I)

wherein X, $R^1$, $R^2$, $R^3$, $R^4$, $R^5$ and $R^6$ are as described in the specification, processes for the preparation of and pharmaceutical compositions comprising said derivatives. The compounds of the present invention are useful for the treatment of epilepsy.

The invention is further directed to a process for the preparation of compounds of formula (XX), wherein X, $R^3$, $R^4$, $R^5$ and $R^6$ are as described in the specification.

34 Claims, No Drawings

OTHER PUBLICATIONS

Kochetkov, N.K. et al., Monosaccharides XXIX. New Variants of the Synthesis of Sulfamates with the Aid of Ethyl Ethynyl Ether, Reports of the USSR Academy of Sciences, 1974, vol. 21b, No. 1, pp. 871-875.

Maryanoff, B.E. et al.: Structure-Activity Studies on Anticonvulsant Sugar Sulfamates Related to Topiramate. Enhanced Potency with Cyclic Sulfate Derivatives: Journal of Medicinal Chemistry, American Chemical Society. Washington, U.S. vol. 41, No. 8, 1998, pp. 1315-1343. XP002149867.

Maryanoff, B.E. et al.: "Synthesis of Phosphates and Phosphate Isosterres of Furanose Sugars as Potential Enzyme Inhibitors", Tetrahedron, vol. 44, No. 11, (1988) pp. 3093-3106.

Maryanoff, B.E. et al.: "Anticonvulsant O-Alkyl Sulfamates. 2,3:4,5-Bis-O-(1-methylethylidene)β-D-fructopyranose Sulfamate and Related Compounds" J. Med. Chem. 1987, 30, 880-887.

Maryanoff, B.E. et al.: "Anticonvulsant Sugar Sulfamates. Potent Cyclic Sulfate and Cyclic Sulfite Analogues of Topiramate", Biorganic & Medicinal Chemistry Letters, vol. 3, No. 12, pp 2653-2656, 1993.

Naidoo, N. T., et al.: Nucleophilic substitution reactions of sugar chlorosulphates with potassium azide[1], S. Afr Journal Chem1986,39(4) pp 208-212.

Naidoo, N.T. et al.: The Synthesis of sugar azidosulphates and azidodeoxy sugars from sugar chlorosulphates, Carbohydrate Research, 62(1978)C5-C6.

G.H. Posner, et al.: Organic Reactions at Alumina Surfaces. A Mechanistic and Synthetic Study of Sulfonate Ester Elimination Reactions Efffected by Chromatographic Alumina:. Journal of Organic Chemistry, vol. 42, No. 1977, pp. 3173-3180, XP002261299.

J-M. Vatele, et al.: "Design and Reactivity of Organic Functional Groups—Preparation and Nucleophilic Displacement Reactions of Imimdazole-1-Sulfonates (Imidazylates)." Tetrahedron, vol. 52, No. 32, (1996) pp. 10557-10568, XP002261300.

Kochetkov, N.K., General Method of Synthesizing Monosaccharide Amidosultates, Reports of the USSR Academy of Sciences 1974, vol. 216, No. 1, pp. 96-100.

Faught et al., abstract Epilepsia, vol. 36, Suppl 4, 1995 pp33.

Copy of International Search Report for International Appl. No. PCT/US 03/14798 dated Dec. 12, 2003.

SUBSTITUTED SULFAMATE ANTICONVULSANT DERIVATIVES

CROSS REFERENCE TO RELATED APPLICATION

This application claims the benefit of U.S. Provisional Application 60/378,017, filed on May 13, 2002, which is incorporated by reference herein in its entirety.

FIELD OF THE INVENTION

The present invention relates to novel anticonvulsant derivatives of the general formula (I):

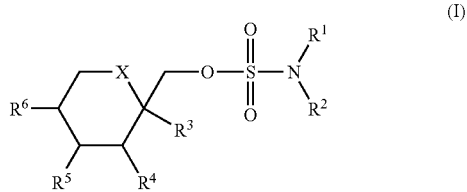

wherein $R^1$, $R^2$, $R^3$, $R^4$, $R^5$, $R^6$ and X are as herein defined, and pharmaceutical compositions containing said derivatives. The compounds of formula (I) are useful in the treatment of epilepsy.

The present invention is further directed to a process for the preparation of compounds of formula (XX)

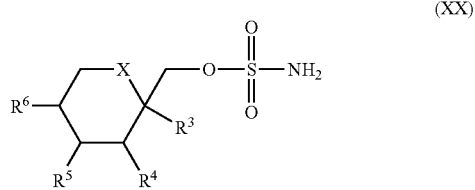

wherein X, $R^3$, $R^4$, $R^5$ and $R^6$ are as herein defined.

The present invention is further directed to compounds prepared according to any of the processes described herein.

BACKGROUND OF THE INVENTION

Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at approximately 0.3 to 0.5 percent in different populations throughout the world, with the prevalence of epilepsy estimated at 5 to 10 people per 1000.

An essential step in the evaluation and management of a patient with a seizure is to determine the type of seizure that has occurred. The main characteristic that distinguishes the different categories of seizures is whether the seizure activity is partial (synonymous with focal) or generalized.

Partial seizures are those in which the seizure activity is restricted to discrete areas of the cerebral cortex. If consciousness is fully preserved during the seizure, the clinical manifestations are considered relatively simple and the seizure is termed a simple-partial seizure. If consciousness is impaired, the seizure is termed a complex-partial seizure. An important additional subgroup comprises those seizures that begin as partial seizures and then spread diffusely throughout the cortex, which are known as partial seizures with secondary generalization.

Generalized seizures involve diffuse regions of the brain simultaneously in a bilaterally symmetric fashion. Absence or petit mal seizures are characterized by sudden, brief lapses of consciousness without loss of postural control. Atypical absence seizures typically include a longer duration in the lapse of consciousness, less abrupt onset and cessation, and more obvious motor signs that may include focal or lateralizing features. Generalized Tonic-clonic or grand mal seizures, the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10–20 s, the tonic phase of the seizure typically evolves into the clonic phase, produced by the superimposition of periods of muscle relaxation on the tonic muscle contraction. The periods of relaxation progressively increase until the end of the ictal phase, which usually lasts no more than 1 min. The postictal phase is characterized by unresponsiveness, muscular flaccidity, and excessive salivation that can cause stridorous breathing and partial airway obstruction. Atonic seizures are characterized by sudden loss of postural muscle tone lasting 1–2 s. Consciousness is briefly impaired, but there is usually no postictal confusion. Myoclonic seizures are characterized by a sudden and brief muscle contraction that may involve one part of the body or the entire body. (www.harrisonsonline.com, Mar. 29, 2001)

U.S. Pat. No. 4,513,006 discloses a class of novel anti-epileptic compounds. One of these compounds, 2,3:4,5-bis-O-(1-methylethylidene)-β-D-fructopyranose sulfamate, known as topiramate, has been demonstrated in clinical trials of human epilepsy to be effective as adjunctive therapy or as monotherapy in treating simple and complex partial seizure and secondarily generalized seizures (E. Faught, B. J. Wilder, R. E. Ramsey, R. A. Reife, L. D. Kramer, G. Pledger, R. M. Karim, et al., *Epilepsia,* 36 (S4) 33, (1995); S. K. Sachdeo, R. C. Sachdeo, R. A. Reife, P. Lim and G. Pledger, *Epilepsia,* 36 (S4) 33, (1995)).

BRIEF SUMMARY OF THE INVENTION

The present invention relates to novel compounds of the formula (I)

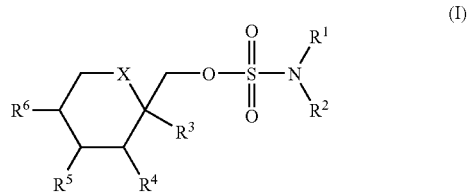

wherein

X is selected from $CH_2$ or O;

$R^1$ is selected from the group consisting of hydrogen, alkyl, alkenyl, alkynyl, cycloalkyl, cycloalkyl-alkyl, cycloalkenyl, aryl, aralkyl, heteroaryl, heteroaryl-alkyl, heterocycloalkyl, heterocycloalkyl-alkyl, alkoxycarbonylalkyl, —($C_{2-8}$alkyl)-O—C(O)-(alkyl), —C(O)—$R^9$, —C(O)-

(alkyl)-O-(alkyl), alkoxycarbonyl, aryloxycarbonyl, aralkyloxycarbonyl, —Si($R^{10}$)($O_{0-1}R^{11}$)$_2$, —$SO_2R^{12}$ and SEM;

wherein the alkyl, cycloalkyl, aryl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^2$ is selected from the group consisting of hydroxy, alkyl, alkoxy, alkenyl, alkynyl, cycloalkyl, cycloalkyl-alkyl, cycloalkenyl, aryl, aryloxy, aralkyl, aralkyloxy, heteroaryl, heteroaryl-alkyl, heterocycloalkyl, heterocycloalkylalkyl, alkoxycarbonylalkyl, —($C_{2-8}$alkyl)-O—C(O)-(alkyl), —C(O)—$R^9$, —C(O)-(alkyl)-O-(alkyl), alkoxycarbonyl, aryloxycarbonyl, aralkyloxycarbonyl, —C(O)O—Si($R^{17}$)$_3$, —Si($R^{10}$)($O_{0-1}R^{11}$)$_2$, —$SO_2R^{12}$, —P(=O)($R^{13}$)$_2$ and SEM;

wherein the alkyl, cycloalkyl, aryl, aralkyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{12}$ is independently selected from amino, alkylamino, dialkylamino, alkyl, aryl, aralkyl or heteroaryl; wherein the alkyl, aryl or heteroaryl groups, whether alone or as part of an $R^{12}$ substituent group, is optionally substituted with one or more substituents independently selected from halogen, trifluoromethyl, trifluoromethoxy, alkyl, alkoxy, nitro, amino, alkylamino, dialkylamino, alkylcarbonylamino, arylcarbonylamino, aralkylcarbonylamino, aryl, heteroaryl, benzenesulfonyl or phenoxy; wherein the phenoxy group is optionally substituted with one or more substituents independently selected from halogen, alkyl, alkoxy or nitro;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively, $R^1$ and $R^2$ are taken together with the N atom to which they are bound to form a heteroaryl or heterocycloalkyl group; wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH) alkylamino or —C(=NH)-dialkylamino; wherein the aryl substiutent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH)-amino, —C(=NH)-alkylamino or —C(=NH)-dialkylamino group is bound to the aryl, heteroaryl or heterocycloalkyl;

alternatively $R^1$ and $R^2$ are taken together with the nitrogen atom to which they are bound to form —N=C($R^{14}$)$_2$;

wherein each $R^{14}$ is independently selected from hydrogen, cycloalkyl, alkyl, dialkylamino, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

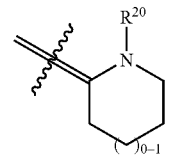

wherein $R^{20}$ is lower alkyl;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

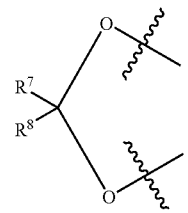

wherein $R^7$ and $R^8$ are the same or different and are hydrogen, lower alkyl or are alkyl and are joined to form a cyclopentyl or cyclohexyl ring;

provided that when $R^1$ is alkyl, $R^2$ is other than alkyl;

provided further that when $R^1$ is hydrogen, $R^2$ is other than alkyl, methylcarbonyl, phenyl, benzyl or carboxyalkyl;

provided further that $R^1$ and $R^2$ when taken together with the nitrogen atom to which they are bound is other than imidazolyl;

provided further that when X is O, $R^2$ and $R^3$ are taken together to form a methylenedioxy group of the formula:

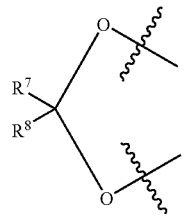

$R^4$ and $R^5$ are taken together to form a methylenedioxy group of the formula:

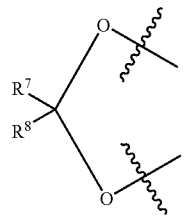

wherein $R^7$ and $R^8$ in each instance are each methyl, and $R^1$ is hydrogen then $R^2$ is other than isopropylsulfonyl, 4-(N-benzyl)-piperidinyl or 4-pyridyl;

or a pharmaceutically acceptable salt thereof.

Illustrative of the invention is a pharmaceutical composition comprising any of the compounds described herein and a pharmaceutically acceptable carrier.

Exemplifying the invention is a pharmaceutical composition made by combining any of the compounds described herein and a pharmaceutically acceptable carrier.

An example of the invention is a process for making a pharmaceutical composition comprising combining any of the compounds described herein and a pharmaceutically acceptable carrier.

Illustrating the invention is a method of treating epilepsy comprising administering to a subject in need thereof a therapeutically effective amount of any of the compounds or pharmaceutical compositions described herein.

Illustrative of the invention is the use of the compounds described herein in the preparation of a medicament for treating epilepsy in a subject in need thereof.

The present invention is further directed to a process for the preparation of a compound of formula (XX)

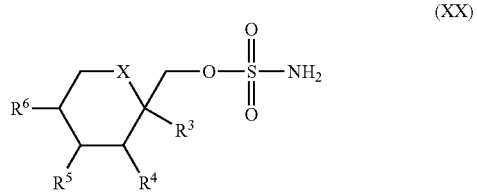

wherein

X is selected from $CH_2$ or O;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

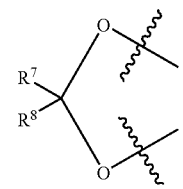

wherein $R^7$ and $R^8$ are same or different and are hydrogen, lower alkyl or are alkyl and are joined to form a cyclopentyl or cyclohexyl ring;

or a pharmaceutically acceptable salt thereof;

comprising, reacting a compound of formula (Ij)

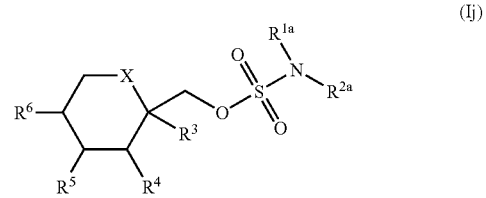

wherein

X is selected from $CH_2$ or O;

$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —Si($R^{10}$)($O_{0-1}R^{11}$)$_2$, and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si($R^{17}$)$_3$, —Si($R^{10}$)($O_{0-1}R^{11}$)$_2$, —P(=O)($R^{13}$)$_2$ and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

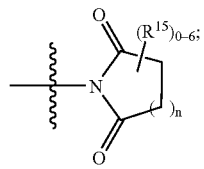

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydtoxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C $(R^{14})_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano;

provided that at least one $R^{14}$ is selected from the group consisting of hydrogen and alkyl;

alternatively, two $R^{14}$ groups are taken together with the carbon atom to which they are bound to form a heterocycloalkyl group of the formula

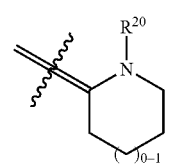

wherein $R^{20}$ is lower alkyl;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

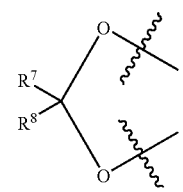

wherein $R^7$ and $R^8$ are same or different and are hydrogen, lower alkyl or are alkyl and are joined to form a cyclopentyl or cyclohexyl ring;

or a pharmaceutically acceptable salt thereof;

under de-protection conditions, to yield the corresponding compound of formula (XX).

The present invention is further directed to a product prepared according to any of the processes described herein.

DETAILED DESCRIPTION OF THE INVENTION

The present invention is directed to a compound of formula (I)

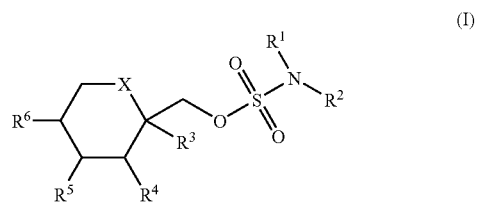

wherein $R^1$, $R^2$, $R^3$, $R^4$, $R^5$, $R^6$ and X are as previously defined, useful for the treatment of epilepsy.

In an embodiment of the present invention is a compound of the formula (I)

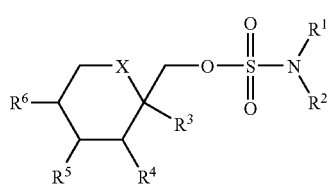

wherein

X is selected from CH$_2$ or O;

R$^1$ is selected from the group consisting of hydrogen, alkyl, alkenyl, alkynyl, cycloalkyl, cycloalkyl-alkyl, cycloalkenyl, aryl, aralkyl, heteroaryl, heteroaryl-alkyl, heterocycloalkyl, heterocycloalkyl-alkyl, alkoxycarbonylalkyl, —(C$_{2-8}$alkyl)-O—C(O)-(alkyl), —C(O)—R$^9$, —C(O)-(alkyl)-O-(alkyl), alkoxycarbonyl, aryloxycarbonyl, aralkyloxycarbonyl, —Si(R$^{10}$)(O$_{0-1}$R$^{11}$)$_2$, —SO$_2$R$^{12}$ and SEM;

wherein the alkyl, cycloalkyl, aryl, heteroaryl or heterocycloalkyl group, whether alone or as part of the R$^1$ substituent group, is optionally substituted with one or more substituents independently selected from halogen, hydroxy, carboxy, alkyl, alkoxy, aryl, aralkyl, amino, alkylamino, dialkylamino, nitro or cyano;

R$^2$ is selected from the group consisting of hydroxy, alkyl, alkoxy, alkenyl, alkynyl, cycloalkyl, cycloalkyl-alkyl, cycloalkenyl, aryl, aryloxy, aralkyl, aralkyloxy, heteroaryl, heteroaryl-alkyl, heterocycloalkyl, heterocycloalkylalkyl, alkoxycarbonylalkyl, —(C$_{2-8}$alkyl)-O—C(O)-(alkyl), —C(O)—R$^9$, —C(O)-(alkyl)-O-(alkyl), alkoxycarbonyl, aryloxycarbonyl, aralkyloxycarbonyl, —C(O)O—Si(R$^{17}$)$_3$, —Si(R$^{10}$)(O$_{0-1}$R$^{11}$)$_2$, —SO$_2$R$^{12}$, —P(=O)(R$^{13}$)$_2$ and SEM;

wherein the alkyl, cycloalkyl, aryl, aralkyl, heteroaryl or heterocycloalkyl group, whether alone or as part of the R$^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^9$ is independently selected from alkyl, aryl or aralkyl; wherein the alkyl or aryl group, whether alone or as part of an R$^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each R$^{10}$ is independently selected from hydrogen, alkyl, aryl or aralkyl; wherein the alkyl or aryl group, whether alone or as part of an R$^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^{11}$ is independently selected from alkyl, aryl or aralkyl; wherein the alkyl or aryl group, whether alone or as part of an R$^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each R$^{12}$ is independently selected from alkyl, aryl, aralkyl or heteroaryl; wherein the alkyl, aryl or heteroaryl groups, whether alone or as part of an R$^{12}$ substituent group, is optionally substituted with one or more substituents independently selected from halogen, trifluoromethyl, trifluoromethoxy, alkyl, alkoxy, nitro, alkylcarbonylamino, arylcarbonylamino, aralkylcarbonylamino, aryl, benzenesulfonyl or phenoxy; wherein the phenoxy group is optionally substituted with one or more substituents independently selected from halogen, alkyl, alkoxy or nitro;

wherein each R$^{13}$ is independently selected from alkyl, alkoxy, aryl, aryloxy, aralkyl or aralkyloxy; wherein the alkyl or aryl group, whether alone or as part of an R$^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^{17}$ is independently selected from alkyl, aryl or aralkyl; wherein the alkyl or aryl group, whether alone or as part of an R$^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively, R$^1$ and R$^2$ are taken together with the N atom to which they are bound to form a heteroaryl or heterocycloalkyl group; wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH)alkylamino or —C(=NH)-dialkylamino; wherein the aryl substituent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH) amino, —C(=NH)-alkylamino or —C(=NH)-dialkylamino group is bound to the aryl, heteroaryl or heterocycloalkyl;

alternatively R$^1$ and R$^2$ are taken together with the nitrogen atom to which they are bound to form —N=C(R$^{14}$)$_2$;

wherein each R$^{14}$ is independently selected from hydrogen, alkyl, cycloalkyl, aryl or aralkyl; wherein the alkyl, cycloalkyl or aryl group, whether alone or as part of an R$^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one R$^{14}$ is selected from the group consisting of hydrogen and alkyl;

R$^3$, R$^4$, R$^5$ and R$^6$ are each independently selected from hydrogen or lower alkyl and, when X is CH$_2$, R$^5$ and R$^6$ may be alkene groups joined to form a benzene ring and, when X is O, R$^3$ and R$^4$ and/or R$^5$ and R$^6$ together may be a methylenedioxy group of the formula:

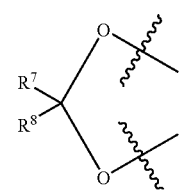

wherein R$^7$ and R$^8$ are the same or different and are hydrogen, lower alkyl or are alkyl and are joined to form a cyclopentyl or cyclohexyl ring;

provided that when $R^1$ is alkyl, $R^2$ is other than alkyl;

provided further that when $R^1$ is hydrogen, $R^2$ is other than alkyl, methylcarbonyl, phenyl, benzyl or carboxyalkyl;

provided further that $R^1$ and $R^2$ when taken together with the nitrogen atom to which they are bound is other than imidazolyl;

provided further that when X is O, $R^2$ and $R^3$ are taken together to form a methylenedioxy group of the formula:

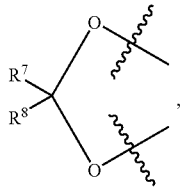

$R^4$ and $R^5$ are taken together to form a methylenedioxy group of the formula:

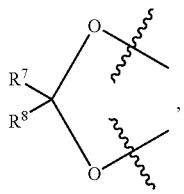

wherein $R^7$ and $R^8$ in each instance are each methyl, and $R^1$ is hydrogen then $R^2$ is other than isopropylsulfonyl, 4-(N-benzyl)-piperidinyl or 4-pyridyl;

or a pharmaceutically acceptable salt thereof.

In an embodiment of the present invention X is O.

In another embodiment of the present invention $R^3$ and $R^4$ and $R^5$ and $R^6$ are taken together as methylenedioxy groups of the formula

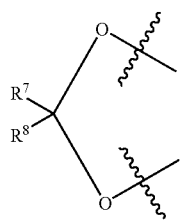

wherein $R^7$ and $R^8$, in each instance, are both hydrogen or are both lower alkyl. Preferably $R^7$ and $R^8$ are both hydrogen or methyl.

In an embodiment of the present invention is a compound of formula (I) wherein X is O, $R^3$ and $R^4$ and $R^5$ and $R^6$ are taken together as methylenedioxy groups of the formula

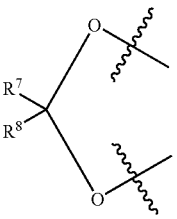

wherein $R^7$ and $R^8$, in each instance, are each lower alkyl, preferably methyl.

In another embodiment of the present invention is a compound of formula (It)

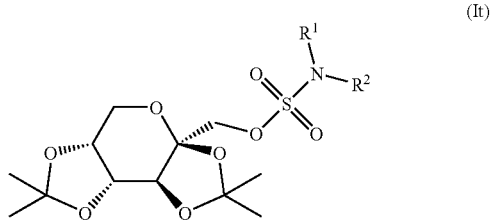

wherein $R^1$ and $R^2$ are as previously defined.

In an embodiment of the present invention $R^1$ is selected from the group consisting of hydrogen, lower alkyl and aralkyl, preferably $R^1$ is hydrogen, methyl or benzyl. In another embodiment of the present invention $R^1$ is hydrogen or lower alkyl, preferably $R^1$ is hydrogen, methyl or ethyl. In yet another embodiment of the present invention, $R^1$ is hydrogen.

In an embodiment of the present invention $R^2$ is selected from the group consisting of hydroxy, alkyl, benzhydryl, alkoxy, alkenyl, aryl, aralkyl, aralkyloxy, alkoxycarbonylalkyl, —C(O)—$R^9$, alkoxycarbonyl, aralkyloxycarbonyl, —C(O)-(alkyl)-O-(alkyl), a nitrogen containing heteroaryl, a nitrogen containing heterocycloalkyl, —SO$_2$R$^{12}$, —C(O)O—Si(R$^{17}$)$_3$, —Si(R$^{10}$)(O$_{0-1}$R$^{11}$)$_2$, —P(=O)(R$^{13}$)$_2$ and SEM;

wherein the alkyl, aralkyl, nitrogen containing heteroaryl or nitrogen containing heterocycloalkyl, whether alone or as part of a substituent group, is optionally substituted with one or more substituents independently selected from halogen, hydroxy, carboxy, alkyl, alkoxy, aryl, aralkyl, amino, alkylamino, dialkylamino, nitro or cyano.

In another embodiment of the present invention $R^2$ is selected from the group consisting of hydroxy, halogenated alkyl, benzhydryl, alkoxy, alkenyl, aralkyl (wherein the aralkyl is optionally substituted with a substituent selected from alkoxy), aralkyloxy, alkoxycarbonylalkyl, carboxyalkyl, alkylcarbonyl (wherein the alkyl is optionally substituted with a substituent selected from carboxy or alkoxycarbonyl), arylcarbonyl (wherein the aryl is optionally substituted with a substituent selected from alkyl, alkoxy, alkoxycarbonyl or carboxy), aralkycarbonyl, alkoxycarbonyl, aralkyloxycarbonyl, alkoxyalkylcarbonyl, aminoalkyl, alkylaminoalkyl, dialkylaminoalkyl, a nitrogen containing heteroaryl (preferably the nitrogen containing heteroaryl is other than 4-pyridyl), a nitrogen containing heterocycloalkyl aminosulfonyl (wherein the amino group is optionally substituted with one to two lower alkyl), alkylsulfonyl (wherein the alkyl group is optionally substituted with one to three substituents independently selected from halogen), arylsulfonyl (wherein the aryl group is optionally substituted with one to three substituents independently selected from alkyl, trifluoromethyl, trifluoromethoxy, halogen, alkoxy, alkylcarbonylamino, acetamido, nitro, amino, alkylamino, dialkylamino or 2-chloro-4-nitrophenyoxy), aralkylsulfonyl, biphenylsulfonyl, heteroarylsulfonyl (wherein the heteroaryl is optionally substituted with one to two substituents independently selected from halogen, alkyl, heteroaryl or benzenesulfonyl), benzhydryl, —Si-(aryl)$_3$, —C(O)O—Si(aryl)$_3$, —P(=O)(aryl)$_2$ —P(=O)(alkoxy)$_2$ and SEM.

In another embodiment of the present invention $R^2$ is selected from the group consisting of hydroxy, halogenated alkyl, benzhydryl, alkoxy, alkenyl, alkoxy substituted aralkyl, aralkyloxy, alkoxycarbonylalkyl, substituted alkylcarbonyl (wherein the alkyl portion of the alkylcarbonyl is substituted with a substituent selected from carboxy or alkoxycarbonyl), arylcarbonyl (wherein the aryl is optionally substituted with a substituent selected from alkyl, alkoxy, alkoxycarbonyl or carboxy), aralkycarbonyl, alkoxycarbonyl, aralkyloxycarbonyl, alkoxyalkylcarbonyl, aminoalkyl, alkylaminoalkyl, dialkylaminoalkyl, a nitrogen containing heteroaryl (preferably, the nitrogen containing heteroaryl is other than 4-pyridyl), a nitrogen containing heterocycloalkyl, aminosulfonyl (wherein the amino group is optionally substituted with one to two lower alkyl), alkylsulfonyl (wherein the alkyl group is optionally substituted with one to three substituents independently selected from halogen), arylsulfonyl (wherein the aryl group is optionally substituted with one to three substituents independently selected from methyl, trifluoromethyl, trifluoromethoxy, halogen, alkoxy, methylcarbonylamino, acetamido, nitro, amino, alkylamino, dialkylamino or 2-chloro-4-nitrophenyoxy), aralkylsulfonyl, biphenylsulfonyl, heteroarylsulfonyl (wherein the heteroaryl is optionally substituted with one to two substituents independently selected from halogen, alkyl, heteroaryl or benzenesulfonyl), benzhydryl, —Si-(aryl)$_3$, —C(O)O—Si(aryl)$_3$, —P(=O)(aryl)$_2$,—P(=O)(alkoxy)$_2$ and SEM.

Preferably, $R^2$ is selected from the group consisting of hydroxy, methoxy, allyl, 1-(2-bromo)-ethyl, 1-(2-ethoxycarbonyl)ethyl, methoxycarbonylmethyl, methoxycarbonylethyl, 1-(methoxycarbonyl)-n-propyl, carboxymethyl, 1-(3-carboxy)-n-propyl, 1-(2-carboxy)ethyl, ethoxycarbonyl, t-butoxycarbonyl, benzyloxycarbonyl, methylcarbonyl, ethylcarbonyl, n-propylcarbonyl, isobutylcarbonyl, phenylethylcarbonyl, benzylcarbonyl, phenylcarbonyl, 2-methoxycarbonylphenyl-carbonyl, 2-carboxyphenyl-carbonyl, methoxycarbonyl-ethylcarbonyl, carboxyethylcarbonyl, diethoxy-phosphinyl, triphenylsilyl, triphenylsilyloxycarbonyl, trifluoromethylsulfonyl, dimethylaminoethyl, benzyl, 4-methoxybenzyl, benzyloxy, 3-pyrrolidinyl, SEM, diphenylphosphinyl, benzhydryl, 2-methoxyphenylcarbonyl, 3-methoxyphenylcarbonyl, 4-methoxyphenylcarbonyl, methoxymethylcarbonyl, 2-tolylcarbonyl, 3-tolylcarbonyl, 4-tolylcarbonyl, 5-heptylcarbonyl, aminosulfonyl, 4-trifluoromethoxyphenylsulfonyl, 1-naphthylsulfonyl, 2-naphthylsulfonyl, 1-(5-dimethylamino-naphthyl)-sulfonyl, 4-biphenylsulfonyl, 2-thienylsulfonyl, 2-(3-(2-pyridyl)-thienyl)-sulfonyl, 4-trifluoromethylphenylsulfonyl, 3-trifluoromethylphenylsulfonyl, 2,6-difluorophenylsulfonyl, benzylsulfonyl, 4-methoxyphenylsulfonyl, 4,5-dibromo-2-thienylsulfonyl, 2-benzenesulfonyl-5-thienylsulfonyl, trifluoromethylsulfonyl, 3-trifluoromethylphenylsulfonyl, 2,2,2-trifluoroethylsulfonyl, phenylsulfonyl, 2,4,6-trimethylphenyl-sulfonyl, 2-chloro-1-ethylsulfonyl, isobutylsulfonyl, 1-butylsulfonyl, 4-(2,1,3,-benzoxadiazolyl)sulfonyl, 4-(2-chloro-4-nitrophenoxy)-3,5-dichlorophenylsulfonyl, 4-bromophenylsulfonyl, ethylsulfonyl, 8-quinolinylsulfonyl, 3,5-dimethyl-4-isoxazolylsulfonyl, 4-(2,1,3-benzothidiazolyl)sulfonyl, 1-propylsulfonyl, 4-methylcarbonylamino-phenyl-sulfonyl, 4-acetamidophenylsulfonyl and 4-nitrophenylsulfonyl.

In an embodiment of the present invention $R^2$ is selected from the group consisting of hydroxy, methoxy, allyl, 1-(3-methoxycarbonyl)-n-propyl, 1-(2-carboxy)ethyl, 1-(2-bromo)-ethyl, 1-(2-ethoxycarbonyl)ethyl, methoxycarbonylmethyl, t-butoxycarbonyl, benzyloxycarbonyl, methylcarbonyl, ethylcarbonyl, triphenylsilyl, triphenylsilyloxycarbonyl, trifluoromethylsulfonyl and benzhydryl.

In an embodiment of the present invention $R^2$ is selected from the group consisting of —C(O)—$R^9$, —C(O)-(alkyl)-O-(alkyl) and —SO$_2$R$^{12}$.

In another embodiment of the present invention $R^2$ is —C(O)—$R^9$; wherein $R^9$ is selected from the group consisting of alkyl, aryl, (wherein the aryl group is optionally substituted with a substitent selected from alkyl or alkoxy) and aralkyl. Preferably, $R^9$ is selected from the group consisting of methyl, ethyl, n-propyl, isobutyl, 5-heptyl, phenyl, benzyl, phenylethyl, 2-methoxyphenyl, 3-methoxyphenyl, 4-methoxyphenyl, 2-tolyl, 3-tolyl and 4-tolyl In yet another embodiment of the present invention $R^2$ is —SO$_2$—$R^{12}$; wherein $R^{12}$ is selected from the group consisting of amino, lower alkylamino, di(lower alkyl)amino, alkyl, (wherein the alkyl group, whether alone or as part of a substituent group is optionally substituted with one to three substituents independently selected from halogen), aryl (wherein the aryl group is optionally substituted with one to three substituents independently selected from alkyl, trifluoromethyl, trifluoromethoxy, halogen, alkoxy, methylcarbonylamino, acetamido, nitro, amino, alkylamino, dialkylamino or 2-chloro-4-nitrophenyoxy), aralkyl, biphenyl and hetroaryl (wherein the heteroaryl is optionally substituted with one to two substituents independently selected from halogen, alkyl, heteroaryl or benzenesulfonyl). Preferably, $R^{12}$ is selected from the group consisting of trifluoromethyl, 4-trifluoromethoxyphenyl, 1-naphthyl, 2-naphthyl, 1-(5-dimethylamino-naphthyl), 4-biphenyl, 2-thienyl, 4-trifluoromethylphenyl, 3-trifluoromethylphenyl, 2,6-difluorophenyl, benzyl, 4-methoxyphenyl, 4,5-dibromo-2-thienyl, 2-benzenesulfonyl-5-thienyl, 2-(3-(2-pyridyl)-thienyl), 3-trifluoromethylphenyl, 2,2,2-trifluoroethyl, phenyl, 2,4,6-trimethylphenyl, 2-chloro-1-ethyl, isobutyl, 1-butyl, 4-(2,1,3,-benzoxadiazolyl), 4-(2-chloro-4-nitrophenoxy)-3,5-dichlorophenyl, 4-bromophenyl, ethyl, 8-quinolinyl, 3,5-dimethyl-4-isoxazolyl, 4-(2,1,3-benzothidiazolyl), 1-propyl, 4-methylcarbonylamino-phenyl, 4-acetamidophenyl and 4-nitrophenyl.

In an embodiment of the present invention $R^1$ and $R^2$ are taken together with the nitrogen atom to which they are bound to form a group selected from heteroaryl or heterocycloalkyl; wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH)alkylamino or —C(=NH)-dialkylamino; wherein the aryl substituent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH)-amino, —C(=NH)-alkylamino or —C(=NH)-dialkylamino group is bound to the aryl, heteroaryl or heterocycloalkyl.

Preferably, $R^1$ and $R^2$ are taken together with the nitrogen atom to which they are bound to form a heterocycloalkyl group, a six membered monocyclic heteroaryl group or a nine to ten membered bicyclic heteroaryl group, wherein the heterocycloalkyl or heteroaryl group is optionally substituted as previously defined. More preferably, $R^1$ and $R^2$ are taken together with the nitrogen atom to which they are bound to form a heterocycloalkyl group or a nine to ten membered bicyclic heteroaryl group, wherein the heterocycloalkyl or heteroaryl group is optionally substituted as previously defined. More preferably still, $R^1$ and $R^2$ are taken together with the nitrogen atom to which they are cound to form a group selected from morpholinyl, 1-(2-isopropoxyphenyl)-piperazinyl or isoindole-1,3-dione.

In an embodiment of the present invention, $R^1$ and $R^2$ are taken together with the nitrogen atom to which they are bound to form —N═C($R^{14}$)$_2$; wherein $R^{14}$ is selected from the group consisting of hydrogen, dialkylamino, cycloalkyl and aryl; wherein the cycloalkyl or aryl is optionally substituted with one or more substituents independently selected from halogen, hydroxy, carboxy, alkyl, alkoxy, aryl, aralkyl, amino, alkylamino, dialkylamino, nitro or cyano. Preferably, $R^{14}$ is selected from the group consisting of hydrogen, di(lower alkyl)amino, a three to eight membered monocyclic cycloalkyl and aryl, more preferably $R^{14}$ is selected from the group consisting of hydrogen, dimethylamino, cyclohexyl and phenyl.

In an embodiment of the present invention, $R^1$ and $R^2$ are taken together with the nitrogen atom to which they are bound to form —N═C($R^{14}$)$_2$; wherein the two $R^{14}$ groups are taken together with the carbon atom to which they are bound to form a heterocycloalkyl group of the formula

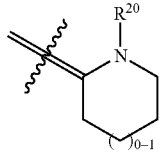

wherein $R^{20}$ is lower alkyl. Preferably, the two $R^{14}$ groups are taken together with the carbon atom to which they are bound to form 2-(1-methyl-pyrrolidinyl).

In an embodiment, the present invention is directed to a compound of the formula (Ij)

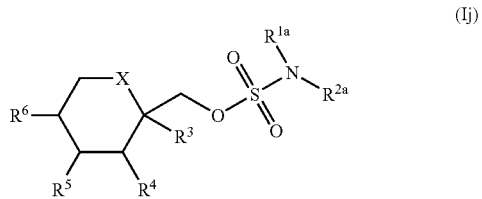

wherein
X is selected from $CH_2$ or O;

$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —Si($R^{10}$)($O_{0-1}$—$R^{11}$)$_2$, and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si($R^{17}$)$_3$, —Si($R^{10}$)($O_{0-1}R^{11}$)$_2$, —P(═O)($R^{13}$)$_2$ and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

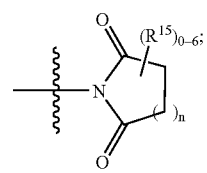

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C$(R^{14})_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

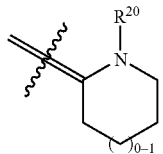

wherein $R^{20}$ is lower alkyl;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

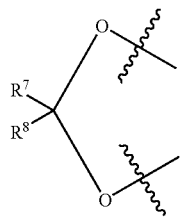

wherein $R^7$ and $R^8$ are same or different and are hydrogen, lower alkyl or are alkyl and are joined to form a cyclopentyl or cyclohexyl ring;

provided than when $R^1$ is hydrogen, then $R^2$ is other than methylcarbonyl or carboxyethyl;

or a pharmaceutically acceptable salt thereof.

In another embodiment of the present invention is a compound of the formula (Ik)

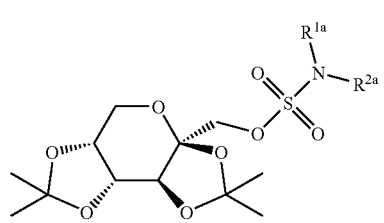

wherein $R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl) —O-(alkyl), alkoxycarbonyl, aryloxycarbonyl, benzyloxycarbonyl, —Si($R^{10}$)($O_{0-1}R^{11}$)$_2$, and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si($R^{17}$)$_3$, —Si($R^{10}$)($O_{0-1}R^{11}$)$_2$, —P(=O)($R^{13}$)$_2$ and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

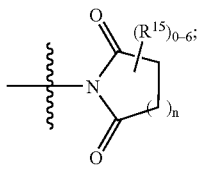

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C$(R^{14})_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

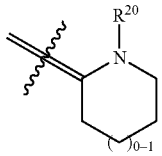

wherein $R^{20}$ is lower alkyl;
provided than when $R^1$ is hydrogen, then $R^2$ is other than methylcarbonyl or carboxyethyl;
or a pharmaceutically acceptable salt thereof.

In an embodiment of the present invention are compounds of formula (Ij) and (Ik) wherein the $R^{1a}$ substituent is a substituent which may be removed under acidic (acid cleavage) de-protection conditions. In another embodiment of the present invention are compounds of formula (Ij) and (Ik) wherein the Ria substituent is a substituent which may be removed under basic de-protection conditions. In yet another embodiment of the present invention are compounds of formula (Ij) and (Ik) wherein the $R^{1a}$ substituent is a substituent which may be removed under catalytic reduction conditions.

In an embodiment of the present invention are compounds of formula (Ij) and (Ik) wherein the $R^{2a}$ substituent is a substituent which may be removed under acidic (acid cleavage) de-protection conditions. In another embodiment of the present invention are compounds of formula (Ij) and (Ik) wherein the $R^{2a}$ substituent is a substituent which may be removed under basic de-protection conditions. In yet another embodiment of the present invention are compounds of formula (Ij) and (Ik) wherein the $R^{2a}$ substituent is a substituent which may be removed under catalytic reduction conditions.

In an embodiment of the present invention are compounds of formula (Ij) and (Ik) wherein $R^{1a}$ and $R^{2a}$ are taken together with the nitrogen atom to which they are bound to form a group which may be removed under de-protection condidions.

The compounds of formula (Ij) and (Ik) are useful as intermediates for the preparation of the corresponding compounds of formula (XX)

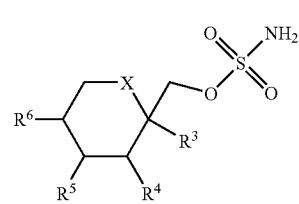

(XX)

wherein X, $R^3$, $R^4$, $R^5$ and $R^6$ are as previously defined, and the compound of formula (XXa)

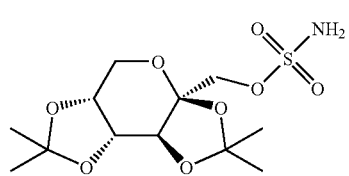

(XXa)

respectively.

The present invention is further directed to a process for the preparation of a compound of formula (XX)

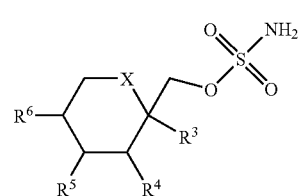

(XX)

wherein X is selected from CH$_2$ or O;
$R^3$, $R^4$, $R^5$ and $R^6$ are each independently selected from hydrogen or lower alkyl and, when X is CH$_2$, $R^5$ and $R^6$ may be alkene groups joined to form a benzene ring and, when X is O, $R^3$ and $R^4$ and/or $R^5$ and $R^6$ together may be a methylenedioxy group of the formula:

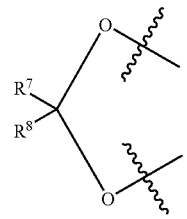

wherein $R^7$ and $R^8$ are the same or different and are selected from hydrogen, lower alkyl or are alkyl and are joined to form a cyclopentyl or cyclohexyl ring;

comprising reacting a compound of formula (Ij)

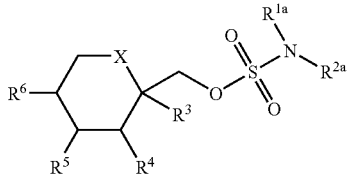

wherein

X is selected from CH$_2$ or O;

R$^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-C$_1$alkyl, heterocycloalkyl-C$_1$alkyl, alkoxycarbonylC$_2$alkyl, —C(O)—R$^9$, —C(O)-(alkyl)-O-(alkyl), alkoxycarbonyl, aryloxycarbonyl, benzyloxycarbonyl, —Si(R$^{10}$)(O$_{0\text{-}1}$R$^{11}$)$_2$, and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the R$^1$ substituent group, is optionally substituted with one or more substituents independently selected from halogen, hydroxy, carboxy, alkyl, alkoxy, aryl, aralkyl, amino, alkylamino, dialkylamino, nitro or cyano;

R$^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-C$_1$alkyl, heterocycloalkyl-C$_1$alkyl, alkoxycarbonylC$_2$alkyl, —C(O)—R$^9$, —C(O)-(alkyl)-O-(alkyl), alkoxycarbonyl, aryloxycarbonyl, benzyloxycarbonyl, —C(O)O—Si(R$^{17}$)$_3$, —Si(R$^{10}$)(O$_{0\text{-}1}$R$^{11}$)$_2$, —P(=O)(R$^{13}$)$_2$ and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the R$^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^9$ is independently selected from alkyl, aryl, aralkyl or heteroaryl; wherein the alkyl, aryl or heteroaryl group, whether alone or as part of an R$^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each R$^{10}$ is independently selected from hydrogen, alkyl, aryl or aralkyl; wherein the alkyl or aryl group, whether alone or as part of an R$^{10}$ substituent group, is optionally substituted with one or more substituents independently selected from halogen, hydroxy, carboxy, alkyl, alkoxy, aryl, amino, alkylamino, dialkylamino, nitro or cyano;

wherein each R$^{11}$ is independently selected from alkyl, aryl or aralkyl; wherein the alkyl or aryl group, whether alone or as part of an R$^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each R$^{13}$ is independently selected from alkyl, alkoxy, aryl, aryloxy, aralkyl or aralkyloxy; wherein the alkyl or aryl group, whether alone or as part of an R$^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^{17}$ is independently selected from alkyl, aryl or aralkyl; wherein the alkyl or aryl group, whether alone or as part of an R$^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively R$^{1a}$ and R$^{2a}$ are taken together with the nitrogen atom to which they are bound to form a group of the formula

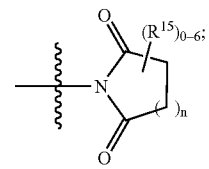

wherein n is an integer from 1 to 3; and wherein each R$^{15}$ is independently selected from the group consisting of halogen, hydroxy, carboxy, alkyl, alkoxy, aryl, aralkyl, amino, alkylamino, dialkylamino, nitro and cyano;

alternatively two R$^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively R$^{1a}$ and R$^{2a}$ are taken together with the nitrogen atom to which they are bound to form —N=C(R$^{14}$)$_2$;

wherein each R$^{14}$ is independently selected from hydrogen, dialkylamino, alkyl, cycloalkyl, aryl or aralkyl; wherein the alkyl, cycloalkyl or aryl group, whether alone or as part of an R$^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one R$^{14}$ is selected from the group consisting of hydrogen and alkyl;

alternatively, two R$^{14}$ groups are taken together with the carbon atom to which they are bound to form a heterocycloalkyl group of the formula

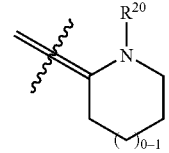

wherein R$^{20}$ is lower alkyl;

R$^3$, R$^4$, R$^5$ and R$^6$ are each independently selected from hydrogen or lower alkyl and, when X is CH$_2$, R$^5$ and R$^6$ may be alkene groups joined to form a benzene ring and, when X is O, $R^3$ and $R^4$ and/or $R^5$ and $R^6$ together may be a methylenedioxy group of the formula:

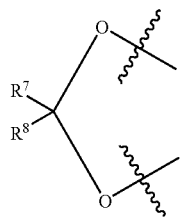

wherein $R^7$ and $R^8$ are same or different and are hydrogen, lower alkyl or are alkyl and are joined to form a cyclopentyl or cyclohexyl ring;

or a pharmaceutically acceptable salt thereof;

under de-protection conditions, to yield the corresponding compound of formula (XX). The compounds of formula (XX) are useful for the treatment of epilepsy.

In an embodiment of the present invention is a process for the preparation of a compound of formula (XX)

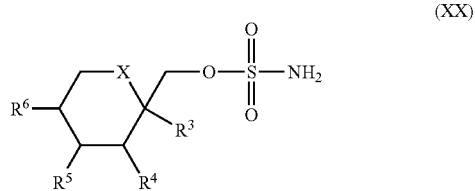

wherein

X is selected from $CH_2$ or O;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

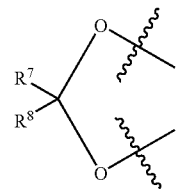

wherein $R^7$ and $R^8$ are same or different and are hydrogen, lower alkyl or are alkyl and are joined to form a cyclopentyl or cyclohexyl ring;

or a pharmaceutically acceptable salt thereof;

comprising, reacting a compound of formula (Ij)

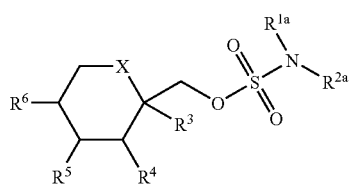

wherein

X is selected from $CH_2$ or O;

$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —Si($R^{10}$)($O_{0-1}R^{11}$)$_2$, and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si($R^{17}$)$_3$, —Si($R^{10}$)($O_{0-1}R^{11}$)$_2$, —P(=O)($R^{13}$)$_2$ and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl or aralkyl; wherein the alkyl or aryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

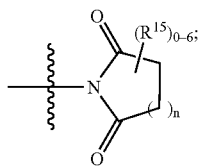

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C$(R^{14})_2$;

wherein each $R^{14}$ is independently selected from hydrogen, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano;

provided that at least one $R^{14}$ is selected from the group consisting of hydrogen and alkyl;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

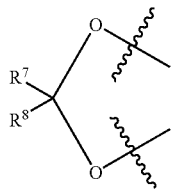

wherein $R^7$ and $R^8$ are same or different and are hydrogen, lower alkyl or are alkyl and are joined to form a cyclopentyl or cyclohexyl ring;

or a pharmaceutically acceptable salt thereof;

under de-protection conditions, to yield the corresponding compound of formula (XX).

In an embodiment of the present invention is a process for the preparation of a compound of formula (XXa)

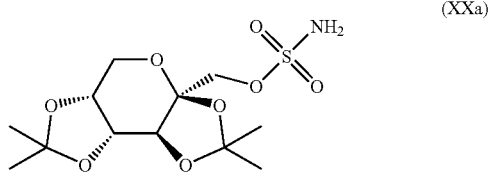

comprising reacting a compound of formula (Ik)

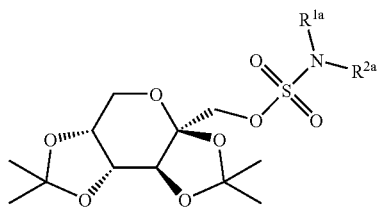

wherein $R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —Si$(R^{10})(O_{0-1}R^{11})_2$, and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si$(R^{17})$ 3, —Si$(R^{10})(O_{0-1}R^{11})_2$, —P(=O)$(R^{13})_2$ and SEM;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

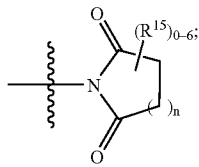

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N═C($R^{14}$)$_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

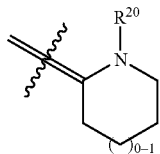

wherein $R^{20}$ is lower alkyl;
or a pharmaceutically acceptable salt thereof;
under de-protection conditions, to yield the corresponding compound of formula (XXa). The compounds of formula (XXa) are useful for the treatment of epilepsy.

The present invention is further directed to a product prepared by reacting a compound of formula (Ij), as previously defined, under de-protedtion conditions. In an embodiment of the present invention is a product prepared by reacting a compound of formula (Ik), as previously defined, under de-protection conditions.

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Preferably, the alkyl group comprises one to eight carbon atoms. Unless otherwise noted, "lower" when used with alkyl means a carbon chain composition of 1–4 carbon atoms.

As used herein, the term "alkenyl" shall denote partially unsaturated straight and branched alkyl chains containing one or more double bonds, preferably one to two double bonds. Suitable example include allyl, butenyl, propenyl, and the like. Preferably, the double bond on the alkenyl group is at least one carbon atom removed from the attachment point.

Similarly, the term "alkynyl" shall denote partially unsaturated straight and branched alkyl chains containing one or more triple bonds, preferably one to two triples bonds, more preferably one triple bond. Suitable examples include propargyl, —CH$_2$CH$_2$CCH, and the like; wherein the triple bond on the alkenyl group is at least one carbon atom removed from the attachment point.

As used herein, the term "cycloalkyl" shall mean any stable 3 to 8 membered monocyclic or 9 to 14 membered saturated bicyclic ring system. Suitable examples include cyclopropyl, cyclobutyl, cyclopentyl, cyclohexyl, cycloheptyl, cyclooctyl, octahydroindenyl, decahydronaphthyl, and the like. The term "cycloalkenyl" shall mean any stable 3 to 8 membered monocyclic, partially unsaturated ring system containing one or more double bonds, or any stable 9 to 14 membered, bicyclic, partially unsaturated (i.e. containing one or more double bonds) or partially aromatic ring system. Suitable examples include cyclohexenyl, cyclopentenyl, cyclopropenyl, cyclohex-1,4-dienyl, tetrahydronaphthyl, indanyl, and the like.

As used herein, unless otherwise noted, "aryl" whether used alone or as part of a substituent group, shall refer to a carbocylic aromatic group such as phenyl, naphthyl, and the like.

As used herein, unless otherwise noted, "aralkyl" whether used alone or as part of a substituent group, shall mean any lower alkyl group substituted with an aryl group such as phenyl, naphthyl and the like. Suitable examples include, benzyl, phenylethyl, naphthylmethyl, and the like.

As used herein, unless otherwise noted, "alkoxy" whether used alone or as part of a substituent group, shall denote an oxygen ether radical of the above described straight or branched chain alkyl groups. For example, methoxy, ethoxy, n-propoxy, sec-butoxy, t-butoxy, n-hexyloxy and the like. Similarly, the terms "aryloxy" and "aralkyloxy" shall denote an oxygen ether radical of the above described aryl and aralkyl groups, respectively.

As used herein, unless otherwise noted, "heteroaryl" whether used alone or as part of a substituent group, shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Preferably, the heteroaryl group is attached at any carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolyl, indazolyl, benzofuryl, benzothienyl, benzimidazolyl, benzthiazolyl, benzthidiazolyl, benzoxadiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

Particularly preferred heteroaryl groups include thienyl, 2,1,3-benzoxadiazolyl, 2,1,3-benzothidiazolyl, quinolinyl and isoxazolyl.

As used herein, the term "heterocycloalkyl" whether used alone or as part of a substituent group, shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 2,3-dihydro-1H-isoindole, and the like.

Particularly preferred heterocycloalkyl groups include pyrrolidiny, piperidinyl, morpholinyl, piperazinyl and 2,3-dihydro-1H-isoindole.

With reference to substituents, the term "independently" means that when more than one of such substituents is possible, such substituents may be the same or different from each other.

When a particular group is "substituted" (e.g., phenyl, aryl, aralkyl, heteroaryl), that group may have one or more substituents, prefereably from one to four substituents, more preferably from one to three substituents, more preferably still from one to two substituents.

As used herein, the symbol "▬" shall denote a bond above the plane of the molecule. Similarly, the symbol "⫽⫽⫽⫽⫽" shall denote a bond below the plane of the molecule.

For use in medicine, the salts of the compounds of this invention refer to non-toxic "pharmaceutically acceptable salts." Other salts may, however, be useful in the preparation of compounds according to this invention or of their pharmaceutically acceptable salts.

Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of the invention carry an acidic moiety, or wherein $R^1$ or $R^{1a}$ is hydrogen, suitable pharmaceutically acceptable salts thereof may include alkali metal salts, e.g., sodium or potassium salts; alkaline earth metal salts, e.g., calcium or magnesium salts; and salts formed with suitable organic ligands, e.g., primary, secondary, tertiary or quaternary ammonium salts, such as morpholinyl, t-butylamino, choline, and the like.

Representative pharmaceutically acceptable salts also include the following:

acetate, benzenesulfonate, benzoate, bicarbonate, bisulfate, bitartrate, borate, calcium edetate, camsylate, carbonate, clavulanate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, valerate, benzanthine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who is the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly the Schemes and Examples, are as follows:

| | |
|---|---|
| AcN = | Acetonitrile |
| Benzhydryl = | —CH(phenyl)$_2$ |
| CDI = | 1,1'-carbonyldiimidazole |
| DAF = | Diacetone fructose |
| DCC = | 1,3-Dicyclohexylcarbodiimide |
| DCM = | Dichloromethane |
| DIPEA = | Diisopropylethylamine |
| DME = | Dimethoxyethane |
| DMF = | Dimethylformamide |
| EtOAc = | Ethyl acetate |
| EtOH = | Ethanol |
| GC = | Gas chromatography |
| HBTU = | O-(1H-Benzotriazol-1-yl)-N,N,N',N'-tetramethyluronium hexafluorophosphate |
| HPLC = | High Pressure Liquid Chromatography |
| MeOH = | Methanol |
| SEM = | 2-(Trimethylsilyl)ethoxymethyl |
| SEM—Cl = | 2-(Trimethylsilyl)ethoxymethyl chloride |
| TBAH = | Tetrabutylammonium hydroxide |
| TEA = | Triethylamine |
| THF = | Tetrahydrofuran |
| TLC = | Thin Layer Chromatography |
| Topiramate = | 2,3:4,5-bis-O-(1-methylethylidine)-β-D-fructopyranose sulfamate |

Compounds of formula (I) may be prepared according to the process outlined in Scheme 1.

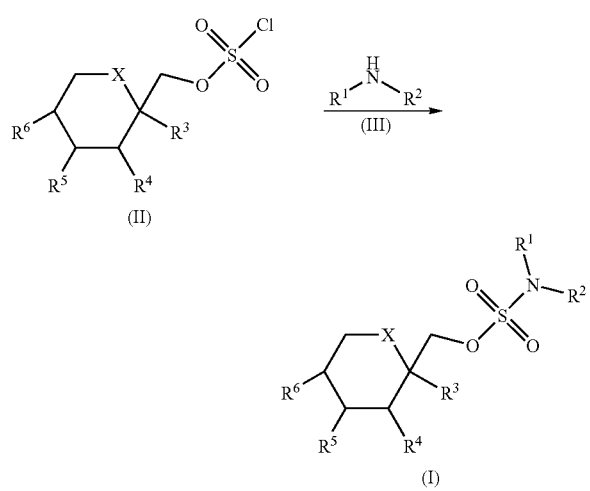

More particularly, a compound of formula (II), a known compound (prepared as disclosed in U.S. Pat. No. 4,513,006, Maryanoff, et al., Issued Apr. 23, 1985) is reacted with a suitably substituted amine of formula (III), a known compound or compound prepared by known methods, preferably in amount in the range of about 1 to about 2 equivalents, in an organic solvent such as acetonitrile, THF, DME, methylene chloride, and the like, in the presence of an organic base such as pyridine, DIPEA, TEA, and the like, to yield the corresponding compound of formula (I).

Alternatively, compounds of formula (I) wherein one of $R^1$ or $R^2$ is selected from hydroxy, alkoxy, aryloxy, or aralkyloxy, may be prepared according to the process outlined in Scheme 2.

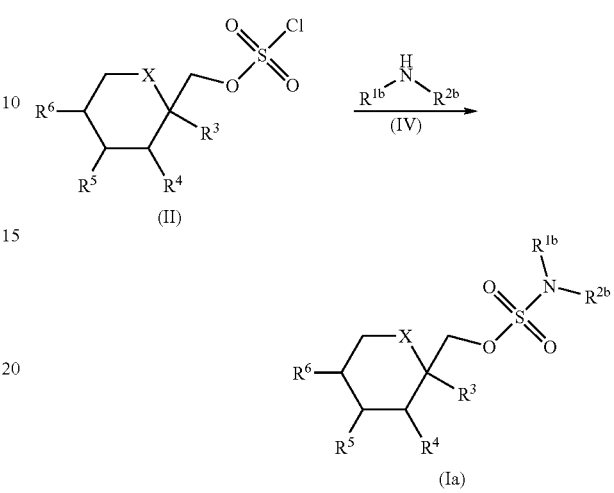

More particularly, a compound of formula (II) is reacted with a suitably substituted compound of formula (IV), wherein one of $R^{1b}$ or $R^{2b}$ is hydroxy, alkoxy, aryloxy, or aralkyloxy, a known compound or compound prepared by known methods, preferably in amount in the range of about 1 to about 2 equivalents, in an organic solvent such as acetonitrile, THF, DME, and the like, in the presence of a base such as $K_2CO_3$, DIPEA, TEA, and the like, preferably $K_2CO_3$, to yield the corresponding compound of formula (Ia).

Compounds of formula (I) wherein one of $R^1$ is hydrogen and $R^2$ is selected from alkoxycarbonyl, aryloxycarbonyl or aralkyloxycarbonyl (i.e where $R^1$ or $R^2$ is —C(O)—O—$R^{16}$, wherein $R^{16}$ is alkyl, aryl or aralkyl), may be prepared according to the process outlined in Scheme 3.

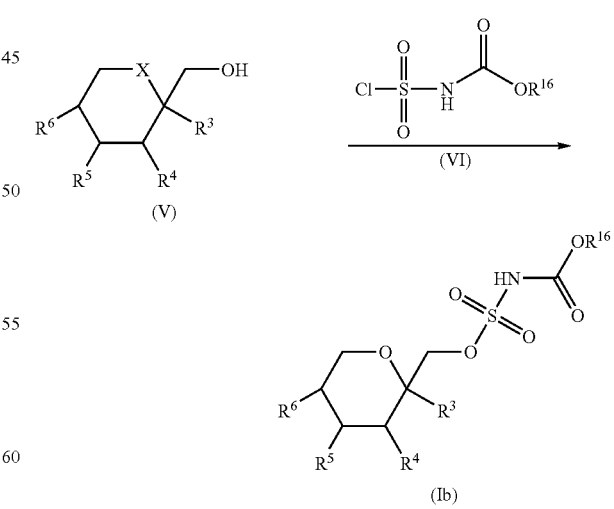

More particularly, a compound of formula (V), a known compound or compound prepared by known methods, is reacted with a suitably substituted compound of formula (VI), wherein $R^{16}$ is selected from alkyl, aryl or aralkyl, a known compound or compound prepared by known methods, in an organic solvent such as acetonitrile, THF, and the like, in the presence of an inorganic base such as sodium hydroxide, $K_2CO_3$, $Na_2CO_3$, $CsCO_3$, and the like or an organic base such as TEA, DIPEA, pyridine, and the like, preferably in the presence of an organic base, to yield the corresponding compound of formula (Ib).

Compounds of formula (I) wherein both $R^1$ and $R^2$ are selected from —C(O)O—$R^{16}$, wherein $R^{16}$ is as previously defined, may be prepared by further reacting the compound of formula (Ib), with a suitably substituted compound of the formula $R^{16}$—O—C(O)—Cl, or a suitably substituted symmetric or asymmetric compound of the formula $R^{16}$—O—C(O)O—O—$R^{16}$, in the presence of a base such as TEA, DIPEA, pyridine, and the like, in an organic solvent such as acetonitrile, THF, and the like.

Alternatively, compounds of formula (I) may be prepared directly from the compound of formula (XX).

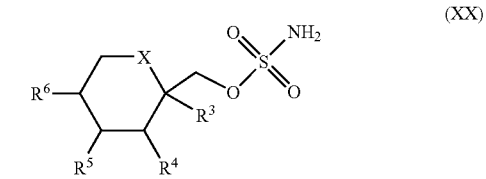

(XX)

Compounds of formula (I) wherein one of $R^1$ or $R^2$ is selected from the group consisting of —C(O)—$R^9$, wherein $R^9$ is as previously defined, may be prepared according to the process outlined in Scheme 4.

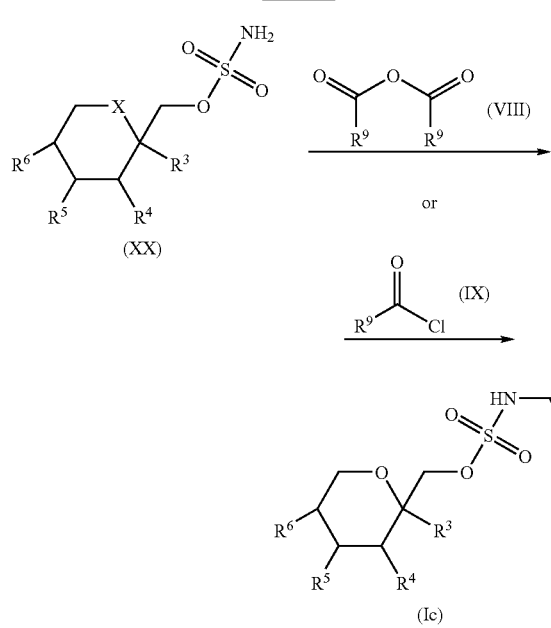

Scheme 4

Accordingly, the compound of formula (XX) is reacted with a suitably substituted symmetric or asymmetric anhydride, preferably a suitably substituted symmetric anhydride, a compound of formula (VIII), a known compound or compound prepared by known methods, wherein $R^9$ is as previously defined, in the presence of an organic base such as TEA, DIPEA, pyridine, and the like, in an organic solvent such as THF, AcN, ethyl acetate, DME and the like, to yield the corresponding compound of formula (Ic).

Alternatively, the compound of formula (XX) is reacted with a suitably substituted acid chloride, a compound of formula (IX), wherein $R^9$ is as previously defined, in the presence of an organic base such as TEA, DIPEA, pyridine, and the like, in an organic solvent such as THF, acetonitrile, ethyl acetate, DME and the like, to yield the corresponding compound of formula (Ic).

One skilled in the art will recognize that in the process outlined in Scheme 4 above, the acid chloride compound of formula (IX) may alternatively be substituted with a suitably substituted acid bromide (i.e a compound of the formula $R^9$—C(O)—Br) or a suitably substituted acid fluoride (i.e a compound of the formula $R^9$—C(O)—F) and reacted with the compound of formula (XX) to yield the corresponding compound of formula (Ic).

Compounds of formula (I) wherein both $R^1$ and $R^2$ are selected from —C(O)—$R^9$, may be prepared by reacting the compound of formula (XX) with at least two equivalents of a suitably substituted acid chloride of formula (IX), according to the process described above.

Alternatively, for compounds of formula (I) wherein both $R^1$ and $R^2$ are each selected from —C(O)—$R^9$ and are not the same, may be prepared by reacting the compound of formula (Ic) with a suitably substituted acid chloride of formula (IX), according to the process described above.

Similarly, compounds of formula (I) wherein one of $R^1$ or $R^2$ is selected from the group consisting of —$SO_2$—$R^{12}$, wherein $R^{12}$ is as previously defined, may be prepared according to the process outlined in Scheme 4, with selection and substitution of a suitably substituted symmetric or asymmetric sulfonic anhydride ($R^{12}$—$SO_2$—O—$SO_2$—$R^{12}$) for the symmetric or asymmetric anhydride of formula (VIII) or selection and substitution of a suitably substituted sulfonyl chloride ($R^{12}$—$SO_2$—Cl) for the acid chloride of formula (IX). One skilled in the art will further recognize that a suitably substituted sulfonyl bromide ($R^{12}$—$SO_2$—Br) may be used in place of the suitably substituted sulfonyl chloride to yield the desired product.

Similarly, compounds of formula (I) wherein one of $R^1$ or $R^2$ is selected from —$SO_2$—$R^{12}$ and $R^{12}$ is selected from the group consisting of amino, alkylamino and dialkylamino, may be prepared by reacting a suitably substituted compound of formula (XX) with sulfuryl chloride ($SO_2Cl_2$) and then reacting with a suitably substituted amine, alkylamine or dialkylamine.

Compounds of formula (I) wherein one or both of $R^1$ or $R^2$ is SEM, may be prepared by reacting the compound of formula (XX) with SEM-Cl, in the presence of a base such as sodium hydride, n-butyl lithium, lithium diisopropylamide, and the like, in an organic solvent such as THF, DME, acetonitrile, ethyl acetate, and the like. Wherein one of $R^1$ or $R^2$ is SEM, the SEM-Cl reagent is present in an amount equal to about 1 equivalent. Wherein when both of $R^1$ and $R^2$ are SEM, the SEM-Cl reagent is present in an amount greater than 1 equivalent, preferably in an amount equal to or greater than about 2 equivalents.

Compounds of formula (I) wherein $R^1$ is —P(O)($R^{13}$)$_2$, wherein $R^{13}$ is as previously defined may be prepared according to the process outlined in Scheme 5.

Scheme 5

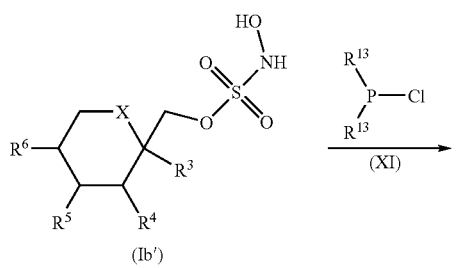

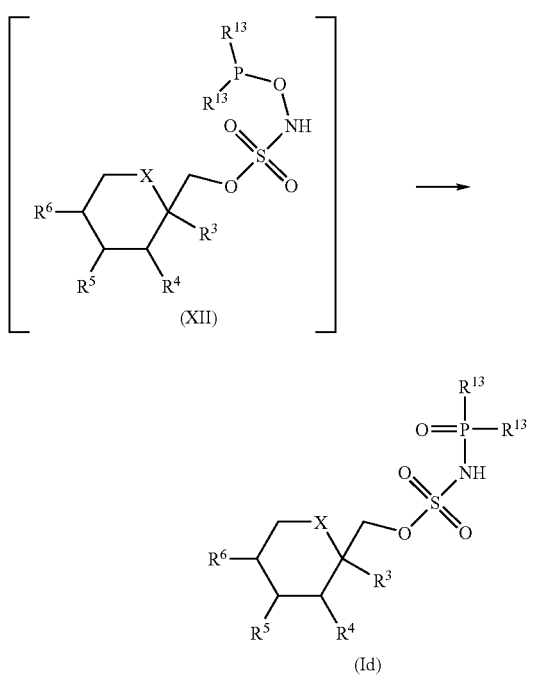

Scheme 6

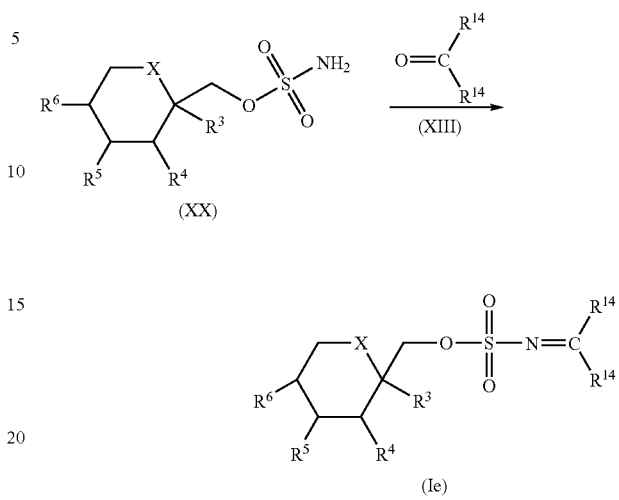

Accordingly, a suitably substituted compound of formula (Ib'), prepared as described in Scheme 2, is reacted with a suitably substituted compound of formula (XI), a known compound or compound prepared by known methods, in the presence of a base such as TEA, DIPEA, pyridine, and the like, in an organic solvent such as toluene, xylene, benzene, and the like, at a reduced temperature, to yield the corresponding compound of formula (XII), which is heated at elevated temperature, preferably at a temperature of greater than or equal to about 80° C., to yield the corresponding compound of formula (Id).

One skilled in the art will recognize that in the process as outlined in Scheme 5 above, a suitably substituted compound of the formula Br—P(R$^{13}$)$_2$ may be substituted for the compound of formula (XI) and reacted with the compound of formula (Ib'), to yield the corresponding compound of formula (XII), which is then further reacted to yield the corresponding compound of formula (Id).

Compounds of formula (I) wherein R$^1$ and R$^2$ are taken together with the N atom to which they are bound to form a group of the formula —N=C(R$^{14}$)$_2$; and wherein at least one R$^{14}$ is selected from the group consisting of hydrogen and alkyl; may be prepared according to the process outlined in Scheme 6.

Accordingly, a suitably substituted compound of formula (XX), a known compound, is reacted with a suitably substituted compound of formula (XIII), a known compound or compound prepared by known methods, in an organic solvent such as MeOH, THF, AcN, and the like, preferably in the presence of a catalytic amount of an acid such as acetic acid, p-toluenesulfonic acid, HCl, and the like, to yield the corresponding compound of formula (Ie).

Similarly, compounds of formula (I) wherein R$^1$ and R$^2$ are taken together with the nitrogen atom to which they are bound to form —N=C(R$^{14}$)$_2$ wherein one R$^{14}$ is dialkylamino, may be prepared by reacting a suitably substituted compound of formula (XX) with a suitably substituted compound of the formula

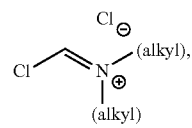

a known compound or compound prepared by known methods, in an organic solvent such as methylene chloride, diethyl ether, THF, and the like.

Similarly, compounds of formula (I) wherein R$^1$ and R$^2$ are taken together with the nitrogen atom to which they are bound to form —N=C(R$^{14}$)$_2$ and wherein two R$^{14}$ groups are taken together with the carbon atom to which they are bound to form a heterocycloalkyl group of the formula

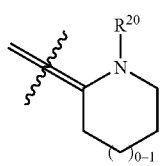

may be prepared by reacting a suitably substituted compound of formula (XX) with a suitably substituted compound of the formula

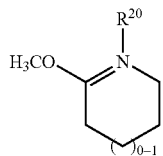

a known compound or compound prepared by known methods, in the presence of base such as sodium hydride, sodium methoxide, sodium ethoxide, and the like, in an organic solvent such as methylene chloride, diethyl ether, THF, and the like.

Compounds of formula (I) wherein $R^1$ and $R^2$ are taken together with the nitrogen atom to which they are bound to form a group of the formula

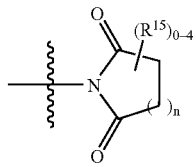

may be prepared according to the process outlined in Scheme 7.

Scheme 7

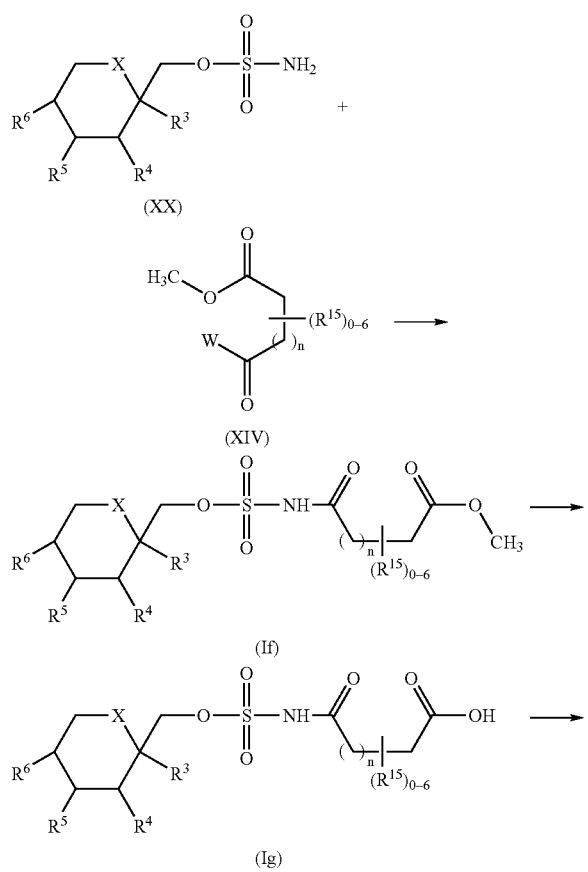

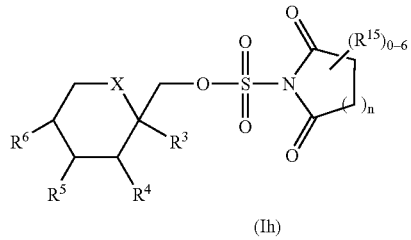

Accordingly, a compound of formula (XX), a known compound or compound prepared by known methods, is reacted with a suitably substituted compound of formula (XIV), wherein W is —OH, —Cl, —Br or —F, a known compound or compound prepared by known methods, in the presence of a coupling agent such as DCC, CDI, HBTU, and the like, in the presence of an organic base such as DIPEA, TEA, pyridine, and the like, in an organic solvent such as DCM, THF, DMF, and the like, or a mixture thereof, to yield the corresponding compound of formula (If). When in the compound of formula (XIV) W is Cl, Br or F, the organic base is an organic tertiary amine base such as TEA, DIPEA, pyridine, and the like.

The compound of formula (If) is reacted with a base such as NaOH, KOH, TBAH, and the like, in a polar organic solvent such as acetone, methanol, DMF, THF, and the like, to yield the corresponding compound of formula (Ig).

The compound of formula (Ig) is subjected to ring closure, in the presence of a coupling agent such as CDI, DCC, HBTU, and the like, in the presence of an organic base such as DIPEA, TEA, pyridine, and the like, in an organic solvent such as THF, DMF, AcN, and the like, to yield the corresponding compound of formula (Ih).

The compounds of formula (XX) may be prepared according to the process outlined in Scheme 8.

Scheme 8

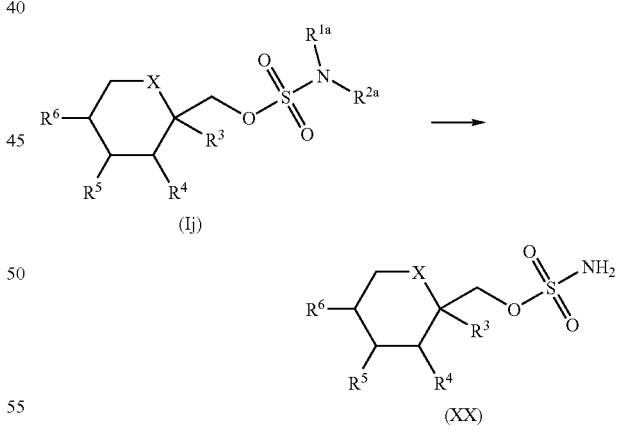

Accordingly, the compound of formula (Ij), prepared as in any of the Schemes described above, is reacted under de-protection conditions (for example as described in T. W. Greene & P. G. M. Wuts, *Protective Groups in Organic Synthesis*, John Wiley & Sons, 1991), to yield the corresponding compound of formula (XX).

For compounds of formula (Ij) wherein $R^{1a}$ is selected from the group consisting of hydrogen, benzyl, heteroaryl-$C_1$alkyl, heterocycloalkyl-$C_1$alkyl and benzyloxycarbonyl; and wherein $R^{2a}$ is selected from the group consisting of benzyl, heteroaryl-$C_1$alkyl, heterocycloalkyl-$C_1$alkyl and benzyloxycarbonyl; the compound of formula (Ij) is subjected to catalytic reduction, to yield the corresponding compound of formula (XX). More particularly, the compound of formula (Ij) is treated with a reducing agent such as $H_2$ gas, preferably hydrogen gas at a pressure of about 1 to about 70 psi, preferably about 50 psi, in the presence of a catalyst such as 10% Pd on carbon, Pt on carbon, and the like, in an organic solvent such as ethanol, methanol, and the like, to yield the corresponding compound of formula (XX).

Alternatively, for compounds of formula (Ij) wherein $R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), alkoxycarbonyl, aryloxycarbonyl, benzyloxycarbonyl, —Si($R^{10}$)($O_{0-1}R^{11}$)$_2$ and SEM; and wherein $R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), alkoxycarbonyl, aryloxycarbonyl, benzyloxycarbonyl, —C(O)O—Si($R^{17}$)$_3$, —Si($R^{10}$)($O_{0-1}R^{11}$)$_2$, —P(=O)($R^{13}$)$_2$ and SEM; or wherein $R^{1a}$ and $R^{2a}$ are taken together with the nitrogen atom to which they are bound to form a group of the formula —N=C($R^{14}$)$_2$; the compound of formula (Ij) is subjected to acid cleavage, to yield the corresponding compound of formula (XX). More particularly, the compound of formula (Ij) is reacted with an acid such as hydrochloric acid, sulfuric acid, trifluoroacetic acid, and the like, in a polar solvent such as acetone, THF, DCM, and the like, preferably acetone, to yield the corresponding compound of formula (XX).

Alternatively still, for compounds of formula (Ij) wherein $R^{1a}$ is selected from the group consisting of hydrogen, alkoxycarbonyl$C_2$alkyl and —C(O)—$R^9$, —C(O)-(alkyl)-O-(alkyl); and $R^{2a}$ is selected from the group consisting of carboxyethyl, alkoxycarbonyl$C_2$alkyl and —C(O)—$R^9$, —C(O)-(alkyl)-O-(alkyl); the compound of formula (I) is subjected to basic cleavage, to yield the corresponding compound of formula (XX). More particularly, the compound of formula (Ij) is reacted with a base such as sodium hydroxide, potassium hydroxide, TBAH, and the like, in an organic solvent such as, THF, DMF, and the like, to yield the corresponding compound of formula (XX).

Compounds of formula (Ij) wherein $R^{1a}$ and $R^{2a}$ are taken together to form a group of the formula

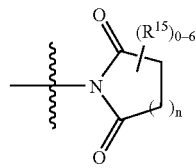

may be reacted under de-protection conditions, to yield the corresponding compound of formula (XX). For example, the compound of formula (Ij) is reacted with a reagent such as hydrazine, methylhydrazine or phenylhydrazine, in an organic solvent such as a lower alcohol (such as ethanol, methanol, isoproanol, and the like), THF, DMF, and the like.

One skilled in the art will recognize that wherein $R^{1a}$ and $R^{2a}$ are independently groups which may not be removed under the same conditions (for example, wherein the $R^{1a}$ group may be removed by acid cleavage and the $R^{2a}$ group may be removed by basic cleavage), the compound of formula (Ij) may be subjected to the individual de-protection conditions required for the $R^{1a}$ and $R^{2a}$ groups, in a sequential or simultaneous manner, to yield the corresponding compound of formula (XX).

In a preferred embodiment of the present invention is a process for the preparation of a compound of formula (XXa) comprising reacting a compound of formula (Ik) under de-protection conditions (for example as described in T. W. Greene & P. G. M. Wuts, *Protective Groups in Organic Synthesis*, John Wiley & Sons, 1991).

In an embodiment of the present invention, the compound of formula (Ij) is de-protected by subjecting the compound of formula (Ij) to catalytic reduction, according to the procedure described above. In another embodiment of the present invention, the compound of formula (Ij) is de-protected by subjecting the compound of formula (Ij) to acidic cleavage, according to the procedure described above. In yet another embodiment of the present invention, the compound of formula (Ij) is de-protected by subjecting the compound of formula (Ij) to basic cleavage, according to the procedure described above. In yet another embodiment of the present invention, the compound of formula (Ij) is de-protected by reacting the compound of formula (Ij) with a reagent such as hydrazine, methylhydrazine or phenylhydrazine, according to the procedure described above.

In an embodiment of the present invention, the compound of formula (Ik) is de-protected by subjecting the compound of formula (Ik) to catalytic reduction, according to the procedure described above. In another embodiment of the present invention, the compound of formula (Ik) is de-protected by subjecting the compound of formula (Ik) to acidic cleavage, according to the procedure described above. In yet another embodiment of the present invention, the compound of formula (Ik) is de-protected by subjecting the compound of formula (Ik) to basic cleavage, according to the procedure described above. In yet another embodiment of the present invention, the compound of formula (Ik) is de-protected by reacting the compound of formula (Ik) with a reagent such as hydrazine, methylhydrazine or phenylhydrazine, according to the procedure described above.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomets by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will further recognize that wherein a reaction step of the present invention may be carried out in a variety of suitable solvents, said reaction step may also be carried out in a mixture of the suitable solvents.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 5 to about 2000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The method of treating epilepsy described in the present invention may also be carried out using a pharmaceutical composition comprising any of the compounds as defined herein and a pharmaceutically acceptable carrier. The pharmaceutical composition may contain between about 1 mg and about 2000 mg, preferably about 5 mg to about 1000 mg, more preferably about 10 mg to about 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolyl-ysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of epilepsy is required.

The daily dosage of the products may be varied over a wide range from 5 to 1,000 mg per adult human per day. For oral administration, the compositions are preferably provided in the form of tablets containing, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 50 mg/kg of body weight per day. Preferably, the range is from about 0.1 mg/kg to about 25 mg/kg of body weight per day, more preferably from about 0.2 mg/kg to about 10 mg/kg, more preferably from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

The following examples describe the invention in greater detail and are intended to illustrate the invention, but not to limit it.

EXAMPLE 1

N-allyl-2,3:4,5-bis-O-(1-methylethylidene)-β-D-fructopyranose sulfamate (Compound #2)

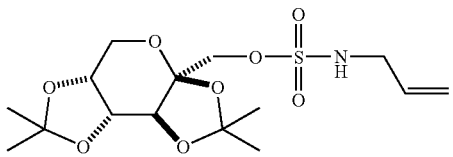

A 500 mL three-necked reaction flask equipped with a thermometer, stirring bar, addition funnel and $N_2$ outlet was charged with allyl amine (2.1 mL, 28 mmol), tetrahydrofuran (85 mL) and triethylamine (4.7 mL, 33.5 mmol). The addition funnel was charged with 2,2,7,7-tetramethyl-tetrahydro-bis[1,3]dioxolo[4,5-b;4'5'-d]pyran-3a-ylmethyl ester chlorosulfuric acid (10.0 g, 28 mmol) and tetrahydrofuran (20 mL) which was slowly added (over 10 minutes) at room temperature. Upon complete addition, the reaction was warmed to 50° C. and stirred for 4 h. The resulting suspension was filtered and concentrated to yield a crude oil. The oil was taken up in ethyl acetate (200 mL) and washed with saturated $NH_4Cl$ (1×50 mL) and brine (1×50 mL). After phase separation, the organic layer was dried over $Na_2SO_4$ (150 g), then filtered and concentrated under vacuum to yield a light yellow oil (9.3 g). The oil was applied to silica gel and eluted with ethyl acetate and hexane (30%) to yield the title compound. Upon standing the compound slowly crystallized to yield a low melting white solid.

m.p. 51–52° C. $^1$H NMR (300 MHz, $CDCl_3$) δ 5.99–5.80 (1H, m), 5.30 (1H, d, J=17.5 Hz), 5.24 (1H, d, J=10.2 Hz), 4.63 (1H, dd, J=8.3, 2.5 Hz), 4.35 (1H, d, J=2.7 Hz), 4.27 (1H, s), 4.19 (2H, dd, J=12.9, 10.5 Hz), 3.93 (1H, dd, J=13.0, 1.9 Hz), 3.83–3.74 (3H, m), 1.56 (3H, s), 1.49 (3H, s), 1.44 (3H, s), 1.36 (3H, s). Elemental Analysis: (T=Theoretical, F=Found) T: C, 47.48; H, 6.64; N, 3.69; O, 33.73; S, 8.45. F: C, 47.52; H, 6.77.

Compounds #3–6, 8, 21–27, 37–39 and 45 were similarly prepared according to the above described procedure with appropriate selection and substitution of a suitably substituted amine for the allyl amine described above.

EXAMPLE 2

N-hydroxy-2,3:4,5-bis-O-(1-methylethylidene)-β-D-fructopyranose sulfamate (Compound #9)

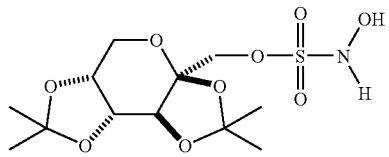

A 250 mL three-necked reaction flask equipped with a thermometer, stirring bar, addition funnel and $N_2$ outlet was charged with hydoxylamine hydrochloride (2.0 g, 29 mmol), tetrahydrofuran (65 mL), water (1.7 mL) and potassium carbonate (3.8 g, 27 mmol). 2,2,7,7-Tetramethyl-tetrahydro-bis[1,3]dioxolo[4,5-b;4'5'-d]pyran-3a-ylmethyl ester chlorosulfuric acid (9.3 g, 26 mmol) in tetrahydrofuran (20 mL) was slowly added (over 10 minutes) via addition funnel at room temperature. Upon complete addition the suspension was stirred for 12 h. The reaction mixture was filtered and concentrated to yield the title product as a white solid.

The product was further purified by recrystallization from tertiary butyl methyl ether/hexane to yield a white solid.

m.p. 45–48° C. $^1$H NMR (300 MHz, $CDCl_3$) δ 7.10 (1H, s), 7.05 (1H, s), 4.62 (1H, dd, J=8.0, 2.5 Hz), 4.35 (1H, d, J=2.6 hz), 4.25 (1H, d, J=7.6 Hz), 3.93 (1H, dd, J=13.0, 1.8 Hz), 3.78 (1H, d, J=12.9 Hz), 3.69 (2H, q, J=17.4, 12.0 Hz), 1.55 (3H, s), 1.49 (3H, s), 1.40 (3H, s), 1.36 (3H, s).

Compounds #10–12 were similarly prepared according to the above described procedure with appropriate selection and substitution of a suitably substituted amine for the hydoxylamine hydrochloride described above.

EXAMPLE 3

N-t-butoxycarbonyl-2,3:4,5-bis-O-(1-methylethylidene)-β-D-fructopyranose sulfamate (Compound #14)

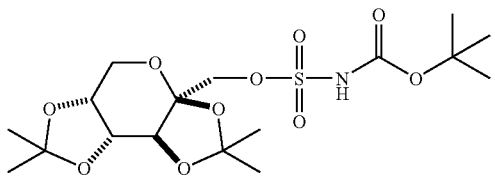

A 100 mL reaction flask equipped with a stirring bar and $N_2$ outlet was charged with chlorosulfonyl isocyanate (1.85 mL, 21 mmol) and dichloromethane (10 mL). At room temperature tertiary butyl alcohol (2.03 mL, 21 mmol) was slowly added and the solution stirred for 30 min. The reaction was then concentrated and the residue taken up in AcN (20 mL). DAF (5.5 g, 21 mmol) in pyridine (2.6 mL, 32 mmol) was then added via addition funnel and the reaction was stirred overnight. The material was then concentrated to dryness to yield an oil. The oil was taken up in DCM (100 mL) and washed with 0.5N HCl (2×50 mL) and brine (1×50 mL). After phase separation, the organic layer was dried over Na$_2$SO$_4$ (150 g), filtered and concentrated under vacuum to yield a light yellow oil (10.5 g). The oil was applied to silica gel and eluted with ethyl acetate and hexane (30%) to yield the title compound as a white powder.

m.p. 88–90° C. $^1$H NMR (300 MHz, CDCl$_3$) δ 4.60 (1H, d, J=7.7 Hz) 4.45–4.34 (2H, m), 4.30–4.19 (2H, m), 3.91 (1H, d, J=12.8 Hz), 3.75 (1H, d, J=13.0 Hz), 1.60–1.38 (18H, m), 1.33 (3H, s) Elemental Analysis: (T=Theoretical, F=Found) T: C, 46.46; H, 6.65; N, 3.19; O, 36.41; S, 7.30. F: C, 46.78; H, 6.89; N, 3.15.

Compound #13 was similarly prepared according to the procedure described above with substitution of triphenyl silynol for tertiary butyl alcohol to yield a white solid.

EXAMPLE 4

N-benzyloxycarbonyl-2,3:4,5-bis-O-(1-methylethylidene)-β-D-fructopyranose sulfamate (Compound #15)

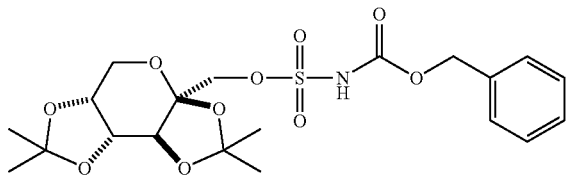

Step A: Preparationn of

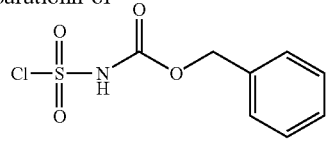

-[[[(chlorosulfonyl)amino]carbonyl]oxy]-benzene

A 250 mL reaction flask equipped with a stirring bar, thermocouple and N$_2$ outlet was charged with chlorosulfonyl isocyanate (10.0 mL, 115 mmol) and dichloromethane (20 mL). After cooling the reaction flask to 0° C. benzyl alcohol (11.9 mL, 115 mmol) was added via addition funnel over 30 min. The internal temperature was kept below 10° C. After complete addition, the reaction mixture was warmed to room temperature, stirred for 15 min, then concentrated under vacuum to yield a white solid. The white solid was triturated in petroleum ether (100 mL). The solid was collected by filtration, washed with petroleum ether (2×50 mL) and dried under vacuum to yield the final product as a fine white powder.

Step B:

A 100 mL reaction flask equipped with a stirring bar and N$_2$ outlet was charged with [[[(chlorosulfonyl)amino]carbonyl]oxy]-benzene (5.0 g, 21 mmol) and acetonitrile (20 mL). Diacetone fructose (5.2 g, 20 mmol) in pyridine (2.4 mL, 30 mmol) was then added via addition funnel and the reaction was stirred overnight. The material was then concentrated to dryness to yield an oil. The oil was taken up in DCM (100 mL) and washed with 0.5N HCl (2×50 mL) and brine (1×50 mL). After phase separation, the organic layer was dried over Na$_2$SO$_4$ (150 g), filtered and concentrated under vacuum to yield a sticky white solid (9.3 g). The material was applied to silica gel and eluted with ethyl acetate and hexane (50%) to yield the title compound as a viscous oil.

$^1$H NMR (300 MHz, CDCl$_3$) δ 8.58 (1H, s), 7.45–7.30 (5H, m), 5.21 (1H, s), 4.58–4.50 (1H, m), 4.42 (1H, dd, J=10.6, 3.0 Hz), 4.35–4.17 (3H, m), 3.87 (1H, d, J=13.4 Hz), 3.74 (1H, d, J=13.2 Hz), 1.51 (3H, s), 1.43 (3H, s), 1.36 (3H, s), 1.32 (3H, s) Elemental Analysis: (T=Theoretical, F=Found) T: C, 50.73; H, 5.75; N, 2.96; O, 33.79; S, 6.77. F: C, 50.97; H, 6.10; N, 2.67.

EXAMPLE 5

N-propanoyl-2,3:4,5-bis-O-(1-methylethylidene)-β-D-fructopyranose sulfamate (Compound #28)

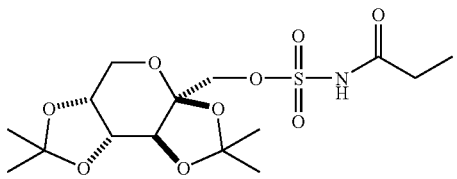

A 200 mL three-necked reaction flask equipped with a stirring bar, addition funnel and N$_2$ outlet was charged with topiramate (3.0 g, 9 mmol), triethylamine (1.5 mL, 11 mmol), tetrahydrofuran (88 mL), propionic anhydride (3.4 mL, 27 mmol) and a catalytic amount of 1,1-dimethylamino pyridine (0.5 g, 4 mmol). The reaction mixture was stirred at room temperature for 16 h, after which time the reaction was quenched with water (200 mL) and ethyl acetate (150 mL). The organic layer was washed with brine (1×100 mL), dried over Na$_2$SO$_4$ (75 g), filtered and concentrated to yield the title compound as a viscous oil.

$^1$H NMR (300 MHz, CDCl$_3$) δ 4.61 (1H, dd, J=8.0, 2.6 Hz), 4.39 (1H, d, J=10.7), 4.33–4.20 (3H, m), 3.90 (1H, d, J=13.4 Hz), 3.76 (1H, d, J=13.4), 2.54–2.34 (2H, m), 1.54 (3H, s), 1.47 (3H, s), 1.42 (3H, s), 1.34 (3H, s), 1.16 (3H, t, J=7.2 Hz) Elemental Analysis: (T=Theoretical, F=Found) T: C, 45.56; H, 6.37; N, 3.54; O, 36.42; S, 8.11. F: C, 45.28; H, 6.47; N, 3.26.

Compound #29 was similarly prepared according to the procedure described above with substitution of acetic anhydride for propionic anhydride, to yield a yellow oil.

Compounds #49–61 were similarly prepared according to the procedure described above with appropriate selection and substitution of a suitably substituted acid chloride for the propionic anhydride.

EXAMPLE 6

N-acetyl-2,3:4,5-bis-O-(1-methylethylidene)-β-D-fructopyranose sulfamate sodium salt (Compound #18)

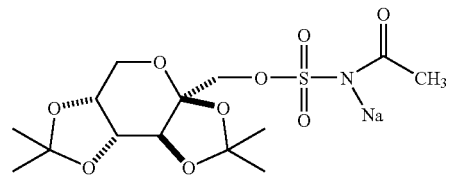

A 200 mL three-necked reaction flask equipped with stirring bar, addition funnel and N$_2$ outlet was charged with sodium hydride (0.2 g, 8 mmol) and tetrahydrofuran (70 mL). A tetrahydrofuran (15 mL) solution of N-acetyl-2,3,4, 5-bis-O-(1-methylethylidine)-β-D-fructopyranose sulfamate (3.2 g, 8 mmol) was added slowly via addition funnel. The mixture was allowed to stir at room temperature for 1 h, after which time the solvent was removed under reduced pressure. The solid was triturated with hexane to yield the product as a solid.

A sample of the solid product was recrystallized from acetone and filtered to yield the title product as a sodium salt, as a fine white powder.

$^1$H NMR (300 MHz, CDCl$_3$) δ 4.54 (1H, dd, J=8.0, 2.7 Hz), 4.35 (1H, d, J=2.7 Hz), 4.21 (1H, d, J=8.2 Hz), 3.89–3.68 (3H, m), 3.56 (1H, d, J=13.3 Hz), 1.70 (3H, s), 1.43 (3H, s), 1.34 (3H, s), 1.27 (3H, s) Elemental Analysis: (T=Theoretical, F=Found) T: C, 41.69; H, 5.50; N, 3.47; Na, 5.70; O, 35.70; S, 7.95. F: C, 41.56; H, 5.89; N, 2.94; Na, 5.93.

Compounds #16, 17, 19 and 20 were similarly prepared according to the procedure described above.

EXAMPLE 7

N-trifluoromethylsulfonyl-2,3:4,5-bis-O-(1-methyl-ethylidene)-β-D-fructopyranose sulfamate (Compound #30)

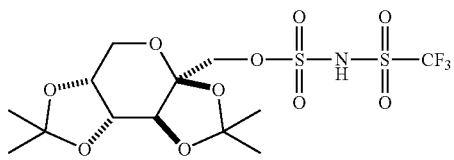

A 100 mL reaction flask equipped with a stirring bar and N$_2$ outlet was charged with topiramate (3.0 g, 9 mmol), pyridine (0.8 mL, 10 mmol) and tetrahydrofuran (10 mL). At room temperature, N-trifluoromethane sulfonyl chloride (0.94 mL, 9 mmol) was added dropwise and stirred for 2.5 h. The reaction was quenched by addition of 1.0 N HCl (50 mL) and extracted with ethyl acetate (100 mL). After phase separation, the organic layer was washed with brine (1×50 mL), dried over Na$_2$SO$_4$ (100 g), filtered and concentrated under vacuum to yield a sticky white solid (3.0 g). The solid was recrystallized from hexane/ether to yield the title compound as a white powder.

m.p. 126° C. $^1$H NMR (300 MHz, CDCl$_3$) δ 4.63 (1H, dd, J=8.0, 2.7 Hz), 4.36–4.2 (4H, m), 3.93 (1H, d, J=13.0, 1.9 Hz), 3.80 (1H, d, J=13.0 Hz), 1.56 (3H, s), 1.51 (3H, s), 1.44 (3H, s), 1.37 (3H, s) Elemental Analysis: (T=Theoretical, F=Found) T: C, 33.12; H, 4.28; N, 2.97; O, 33.94; S, 13.60; F, 12.09. F: C, 33.25; H, 4.18; N, 3.06.

Compounds #44 and 62–91 were similarly prepared according to the procedure described above with appropriate selection and substitution of a suitably substituted chloride for the N-trifluoromethane sulfonyl chloride.

EXAMPLE 8

N-trifluoromethylsulfonyl-2,3:4,5-bis-O-(1-methyl-ethylidene)-β-D-fructopyranose sulfamate morpholinyl salt (Compound #31)

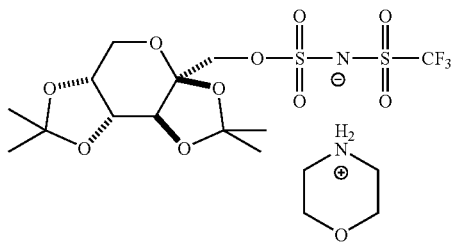

A 50 mL three-necked reaction flask equipped with a stirring bar and N$_2$ outlet was charged with N-trifluorosulfonyl-2,3:4,5-bis-O-(1-methylethylidine)-β-D-fructopyranose sulfamate (0.4 g, 1 mmol), tetrahydrofuran (10 mL), followed by addition of morpholine (0.07 mL, 1 mmol). After stirring for 12 h at room temperature the reaction was concentrated and the resulting solid recrystallized from hexane/ethyl acetate to yield the title product as a water-soluble salt, as an off white solid.

$^1$H NMR (300 MHz, CDCl$_3$) δ 4.70 (8H, s), 4.43–4.37 (2H, m), 4.16 (2H, d, J=3.6 Hz), 3.93 (1H, d, J=13.7 Hz), 3.83 (1H, t, J=5.0 Hz), 3.74 (1H, d, J=13.7 Hz), 1.52 (3H, s), 1.44 (3H, s), 1.38 (3H, s), 1.33 (3H, s)

Compound #32 was similarly prepared according to the procedure described above with substitution of t-butylamine for morpholine, to yield a white solid.

EXAMPLE 9

N,N-di(2-(trimethylsilyl)ethoxymethyl)-2,3:4,5-bis-O-(1-methylethylidene)-β-D-fructopyranose sulfamate (Compound #33)

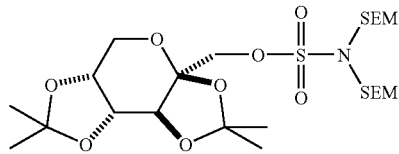

A 100 mL three-necked reaction flask equipped with a stirring bar and N$_2$ outlet was charged with topiramate (1.0 g, 3 mmol), diisopropylethyl amine (0.6 mL, 4 mmol) and tetrahydrofuran (30 mL). At room temperature 2-(trimethylsilyl)ethoxymethyl chloride (SEM-Cl) (0.55 mL, 3 mmol) was added dropwise and stirred for 14 h. The reaction was quenched by addition of saturated ammonium chloride (50 mL) and extracted with ethyl acetate (100 mL). After phase separation, the organic layer was washed brine (1×50 mL), then dried over Na$_2$SO$_4$ (50 g), filtered and concentrated under vacuum to yield a thick oil. The oil material was applied to silica gel and eluted with ethyl acetate and hexane (30%) to yield the title product as the major product, as an oil.

$^1$H NMR (300 MHz, CDCl$_3$) δ 4.76 (4H, s), 4.61 (1H, dd, J=8.0, 2.7 Hz), 4.38 (1H, d, J=3.6 Hz), 4.27–4.24 (1H, m), 4.22 (1H, s), 4.14–4.10 (1 H, m), 3.91 (1H, dd, J=13.0, 2.0 Hz), 3.75 (1H, d, J=12.8 Hz), 3.66–3.57 (4H, m), 1.55 (3H, s), 1.48 (3H, s), 1.41 (3H, s), 1.32 (3H, s), 0.01 (18H, s) Elemental Analysis: (T=Theoretical, F=Found) T: C, 48.05; H, 8.23; N, 2.33; O, 26.67; S, 5.35; Si, 9.36. F: C, 48.33; H, 8.15; N, 2.12.

EXAMPLE 10

N-diphenylphosphinyl-2,3:4,5-bis-O-(1-methylethylidene)-β-D-fructopyranose sulfamate (Compound #34)

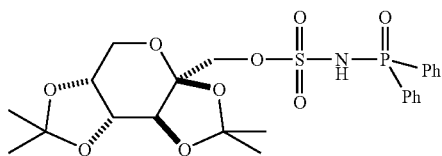

A 50 mL reaction flask equipped with a stirring bar and N₂ outlet was charged with N-hydroxyl topiramate derivative (2.1 g, 6 mmol), triethylamine (0.9 mL, 7 mmol) and toluene (16 mL). The mixture was cooled to 0° C., chlorodiphenylphosphine (1.17 mL, 7 mmol) was added dropwise and the reaction mixture was stirred at room temperature for 1 h. The suspension was filtered through Celite and the filtrate warmed to 80° C. for 14 h. The vessel was cooled and the reaction mixture concentrated to dryness, resulting in a white solid which was recrystallized from tertiary butyl methyl ether to yield the title product as a white solid.

m.p. 137–138° C. ¹H NMR (300 MHz, CDCl₃) δ 7.52–7.39 (4H, m), 7.17–7.00 (6H, m), 4.22 (1H, dd, J=7.9, 2.5 Hz), 3.90–3.86 (1H, m), 3.84 (1H, s), 3.68 (2H, dd, J=16.1, 9.9 Hz), 3.49 (1H, dd, J=13.0, 1.8 Hz), 3.24 (3H, d, J=13.0 Hz), 1.11 (3H, s), 0.98 (3H, s), 0.96 (3H, s), 0.89 (3H, s) Elemental Analysis: (T=Theoretical, F=Found) T: C, 53.43; H, 5.60; N, 2.60; O, 26.69; P, 5.74; S, 5.94. F: C, 53.72; H, 5.42; N, 2.33.

EXAMPLE 11

N-(4-carboxy-1-propyl)-2,3:4,5-bis-O-(1-methylethylidene)-β-D-fructopyranose sulfamate (Compound #7)

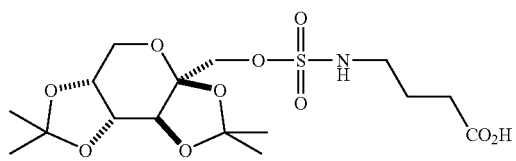

A 50 mL reaction flask equipped with a stirring bar and N₂ outlet was charged with methylbutyrate, 2,3:4,5-bis-O-(1-methylethylidene)-β-D-fructopyranose sulfamate (0.79 g, 2 mmol) and acetone (6 mL). 1.0N sodium hydroxide (1.9 mL, 1.9 mmol) was added to the solution and the reaction mixture was stirred at room temperature for 15 min. The acetone was removed under vacuum. Ethyl acetate (50 mL) was then added and the pH adjusted to about pH 3, with 1.0 N HCl. The layers were separated, the organic layer was dried over Na₂SO₄ (25 g), filtered and concentrated to yield the title compound as a thick oil.

¹H NMR (300 MHz, CDCl₃) δ 5.30 (1H, s), 4.63–4.55 (1H, m), 4.35–4.28 (1H, m), 4.23 (1H, d, J=7.6 Hz), 4.12 (2H, q, J=20.4, 11.4 Hz), 3.89 (1H, d, J=12.8 Hz), 3.74 (1H, d, J=12.7 Hz), 3.19 (2H, q, J=12.3, 5.7 Hz), 2.41 (2H, t, J=7.1 Hz), 1.89 (2H, t, J=7.1 Hz), 1.53 (3H, s), 1.45 (3H, s), 1.40 (3H, s), 1.33 (3H, s) Elemental Analysis: (T=Theoretical, F=Found) T: C, 45.17; H, 6.40; N, 3.29; O, 37.61; S, 7.54. F: C, 44.95; H, 6.22; N, 3.05.

Compounds #35 and 36 were similarly prepared according to the procedure described above with appropriate selection and substitution of a suitably substituted ester for the methyl butyrate.

EXAMPLE 12

2,2,7,7,-Tetramethyl-tetrahydro-bis[1,3]dioxolo[4,5-b;4',5'-d]pyran-3a-ylmethyl enzylidene sulfonate (Compound #47)

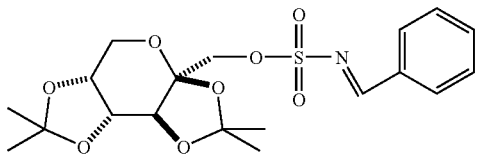

A 100 mL reaction flask equipped with a stirring bar, N₂ outlet and Dean-Stark trap was charged with 2,3:4,5-bis-O-(1-methylethylidine)-β-D-fructopyranose sulfamate (3.39 g, 10 mmol) and toluene (50 mL). Benzaldehyde (1.1 ml, 11 mmol) and 10 drops of acetic acid were added and the reaction was warmed to reflux overnight. The reaction was then cooled and concentrated to yield a thick oil. (Note: The reaction mixture was filtered through Celite prior to concentration on the rotoevaporator to remove any solid particles). The oil was then taken up in EtOAc (150 mL) and washed with NaHCO₃ (2×50 mL). The organics were dried and then filtered through a plug of silica gel (10 g). The eluent was concentrated to yield the title product as a crude oil.

HPLC/MS/ES⁺ [M+1]+ mass=428.0

Compound #46 was similarly prepared according to the procedure described above.

EXAMPLE 13

N-(2-methoxycarbonylphenyl)carbonyl-2,3:4,5-bis-O-(1-methylethylidene)-β-D-fructopyranose sulfamate (Compound #40)

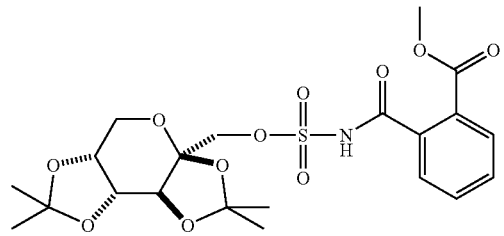

A 300 mL reaction flask equipped with a stirring bar, N₂ outlet and addition funnel was charged with mono-methyl phthalate (5.6 g, 31 mmol) dichloromethane (100 mL) and a drop of DIPEA. The reaction mixture was cooled to 0° C. To the reacion mixture was then added DCC (6.7 g, 32 mmol) and dichloromethane (25 mL), slowly via the addition funnel. The resulting solution was then stirred for 30 minutes at 0° C. To the reaction mixture was then added 2,3:4,5-bis-O-(1-methylethylidine)-β-D-fructopyranose sulfamate (10.0 g, 29 mmol) as a solution of dichloromethane and DIPEA (5.7 mL, 32 mmol). The reaction was allowed to slowly warm to room temperature, with continuing stirring (12 h). The reaction mixture was then concentrated to a thick oil. The oil was taken up in DCM (100 mL) and then washed with 0.5N HCl (2×50 mL) and brine (1×50 mL). The organic layer was separated and dried over $Na_2SO_4$ (150 g), filtered and concentrated under vacuum to yield a light yellow oil. The oil was applied to silica gel and eluted with EtOAc/hexane (60%) to yield the title compound as an oil.

EXAMPLE 14

N-(2-carboxyphenyl)carbonyl-2,3:4,5-bis-O-(1-methylethylidene)-β-D-fructopyranose sulfamate (Compound #41)

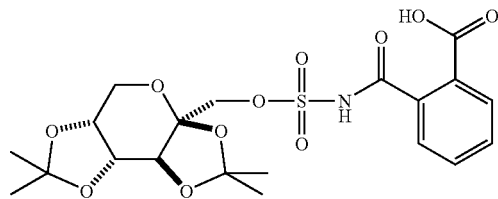

A 100 mL reaction flask equipped with a stirring bar and $N_2$ outlet was charged with compound prepared as in Example 13, (4.0 g, 8 mmol) and acetone (200 mL). NaOH (1.0 M, 20 ml, 20 mmol) was added at room temperature and the reaction was stirred overnight. The reaction was then concentrated and the residual oil taken up in EtOAc (250 mL). After extraction the layers were separated. The aqueous layer was adjusted to about pH 1 with 1.0N HCl (25 mL). The product was extracted with EtOAc (200 mL) and the organic layer dried over $Na_2SO_4$ (150 g), filtered and concentrated under vacuum to yield the title compound as a light yellow oil.

Compounds #42 and 43 were similarly prepared according to the procedure described in Examples 13 and 14 above.

EXAMPLE 15

2,2,7,7,-Tetramethyl-tetrahydro-bis[1,3]dioxolo[4,5-b;4',5'-d]pyran-3a-ylmethyl-1,3,dioxo-1,3-dihydro-isoindole-2-sulfonate (Compound #48)

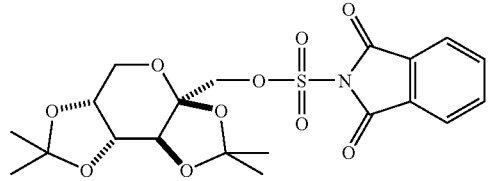

A 100 mL round bottom flask was charged with the compound prepared as in Example 15 (1.2 g, 2.2 mmol) and DMF (25 mL). The reaction vessel was charged with CDI (0.5 g, 3 mmol) and the reaction mixture stirred for one hour at room temperature. To the reaction mixture was then added DIPEA (0.51 mL, 3 mmol) and the reaction continued overnight. The reaction mixture was treated with silica gel (50 g) and filtered through a plug of Celite. Toluene (3×50 mL) was used to wash the pad of Celite and silica gel. The filtrate was concentrated to yield the title compound as a light yellow oil.

HPLC/MS (ES$^+$) [M+Na]$^+$=492.1; [M+K]$^+$=508.2 m/z

EXAMPLE 16

2,3:4,5-bis-O-(1-methylethylidene)-β-D-fructopyranose sulfamate (also known as Topiramate)

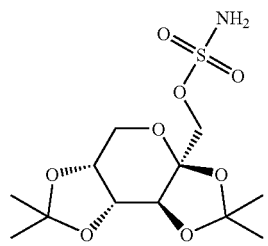

A 250 mL hydrogenation vessel was charged with N-phenoxycarbonyl-2,3:4,5-bis-O-(1-methylethylidene)-β-D-fructopyranose sulfamate (prepared as in Example 4) (1.0 g, 2.1 mmol), ethanol (21 mL) and palladium on carbon (0.1 g, 10% w/w, nominally wet). The vessel was subject to 50 psi $H_2$ using a Parr hydrogenationator at room temperature. After 5 hours the reaction was purged with $N_2$ and filtered through a plug of Celite. The filtrate was concentrated to a thick oil. The oil was treated with ethanol (15 mL) and water (1 mL), and the resulting cloudy mixture was warmed (50° C.) and hot filtered to remove insoluble material. The filtrate was cooled to 0° C. and allowed to crystallize overnight. The solid was collected by filtration, then dried under vacuum to yield the title product as a white solid.

m.p. 126° C.

EXAMPLE 17

2,3:4,5-bis-O (1-methylethylidine)-β-D-fructopyranose sulfamate (also known as Topiramate)

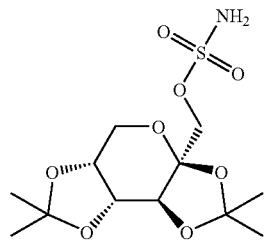

A 20 ml flask was charged with the compound prepared as in Example 12 (0.18 g, 0.42 mmol) and acetone (5 mL). At room temperature a catalytic amount of 2.0N HCl (0.2 mL, 0.2 mmol) was added to the reaction mixture and the resulting light yellow solution was stirred at room temperature. GC and TLC were used to monitor the progress of the reaction. After 1.5 hours the reaction was complete. The reaction mixture was then diluted with EtOAc (1×50 mL) and water (5 mL), the organic layer was separated, dried ($Na_2SO_4$, filtered and concentrated. The product was isolated as a white solid after crystallization from EtOH.

$^1$HNMR of the solid was consistent with topiramate.

EXAMPLE 18

2,3:4,5-bis-O
(1-methylethylidine)-β-D-fructopyranose sulfamate
(also known as Topiramate)

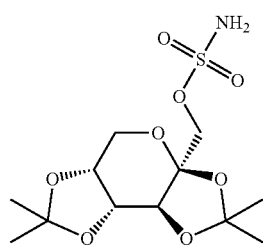

A 20 mL reaction flask equipped with a stirring bar and $N_2$ outlet was charged with N-(2-methoxycarbonylphenyl)carbonyl-2,3:4,5-bis-O-(1-methylethylidine)-β-D-fructopyranose sulfamate, the compound prepared as in Example 13 (0.3 g, 0.6 mmol) and DMF (6 mL). NaOH (3.0 M, 1.2 ml, 3.6 mmol) was added at room temperature. The reaction was warmed to 80° C. and continued overnight (about 12 hrs). The reaction mixture was then cooled to room temperature. 1.0N HCl (10 mL) was added, followed by dilution with EtOAc (75 mL). The layers were separated and the organic layer was dried over $Na_2SO_4$ (10 g), filtered and concentrated to yield the title compound as a thick oil.

$^1$HNMR of the oil was consistent with topiramate.

EXAMPLE 19

N-sulfamoyl-2,3:4,5-bis-O-(1-methylethylidene)-β-D-fructopyranose sulfamate morpholinyl salt
(Compound #100)

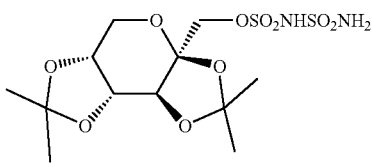

To a cooled (−60° C.) mixture of topiramate (39.02 g, 0.114 mol) and pyridine (18.19 g, 0.23 mol) in THF (300 mL) was added sulfuryl chloride (31.04 g, 0.23 mol), dropwise, over a 10 minute period while maintaining the temperature below −60° C. After 30 minutes, the ice bath was removed and the mixture poured into a 1 L glass lined autoclave. The reactor was pressurized with anhydrous ammonia to 24 psi, ambient temperature, and maintained overnight. The following morning the resulting dark brown mixture was concentrated under reduced pressure and the resulting reddish-brown residue (53.04 g) dissolved in distilled water and extracted with $CH_2Cl_2$ (4×100 mL). The aqueous layer was concentrated under reduced pressure to yield the title compound as a brittle, tan colored foam.

Three separate samples of this foam (6.0 g in 30–40 mL of water, 4.6 g in MeOH and 2.0 g dissolved in the solvent system) were chromatographed on the Waters Prep 500 using a $^{18}$C column, eluting with MeOH:AcN:0.5 M NaCl (15:35:50). The cleanest fractions containing product were combined and concentrated under reduced pressure to yield the product as a tan colored solid.

MS MH$^+$=418

EXAMPLE 20

N-(1-Methyl-pyrrolidin-2-ylidene)-2,3:4,5-bis-O-(1-methylethylidene)-β-D-fructopyranose sulfamate morpholinyl salt (Compound #102)

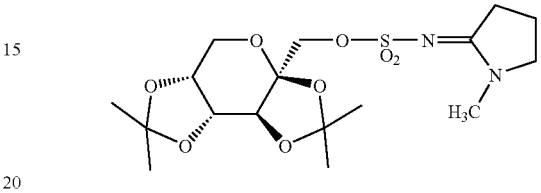

N-Methylpyrrolidione (130.01 g, 1.31 mol) and dimethyl sulfate (153.94 g, 115.5 mL, 1.22 mol) were heated on a steam bath for one hour. The resulting black solution was added to a mixture containing topiramate (104.5 g, 0.31 mol) and sodium methoxide (66.5 g, 1.22 mol) in methylene chloride (660 mL), and then heated at reflux on a steam bath for 4 hr. The reaction mixture was washed with 1 N NaOH (4×100 mL), the layers separated and the aqueous layer extracted with $CH_2Cl_2$ (4×100 mL). The combined organic layer was dried over sodium sulfate, filtered and concentrated under reduced pressure to yield a yellow residue that crystallized on standing. The mixture was filtered and washed with hexane to yield a yellow, crystalline solid. The crude solid was slurried in distilled water and heated on the steam bath. Ethanol was added until a clear solution was obtained. The hot solution was allowed to cool overnight, with stirring. A white precipitate was observed. The mixture was filtered, washed with cold water and dried to yield the title compounds as a white, crystalline solid.

MS MH$^+$=420

EXAMPLE 21

N-(Dimethylaminomethylene)-2,3:4,5-bis-O-(1-methylethylidene)-β-D-fructopyranose sulfamate morpholinyl salt (Compound #103)

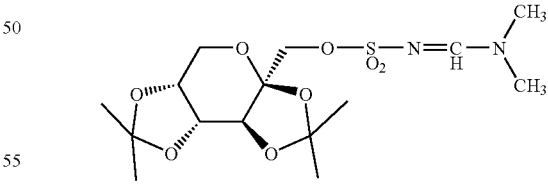

To a stirred solution of N,N-dimethylformamide (26.20 g, 0.358 mol) in diethyl ether (672 mL) was added oxalyl chloride (45.48 g, 0.358 mol), dropwise, over a 35 minute period. A white solid started to precipitate out of solution immediately. The mixture was stirred for 1 hr after the addition was complete then concentrated under reduced pressure to remove the solvent. To this solid was added topiramate (105.54 g, 0.311 mol) dissolved in methylene chloride (800 mL). The yellow solution was stirred at ambient temperature, under argon, for 3 hr then washed with 1 N NaOH (4×100 mL). The aqueous layer was extracted with methylene chloride (4×100 mL). The combined organic layer was dried over sodium sulfate, filtered and concentrated under reduced pressure to yield a thick, yellow residue. The residue was slurried in distilled water (100 mL) while warming on a steam bath, followed by the addition of ethanol (10–15 mL) until a clear solution was obtained. The heat was removed and the solution allowed to cool to ambient temperature, overnight, with stirring. A solid precipitated out of solution. The mixture was filtered and washed with cold water to yield the title product as a white solid.

MS MH+=394.44

EXAMPLE 22

N-2-(5-(2-pyridyl)-thienyl)-2,3:4,5-bis-O-(1-methylethylidene)-β-D-fructopyranose sulfamate morpholinyl salt (Compound #98)

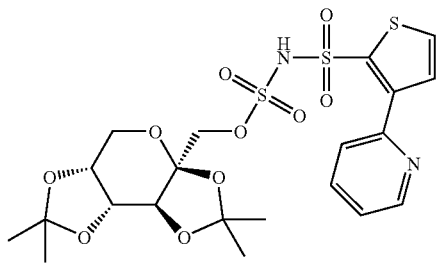

A mixture of topiramate (1.5 gm, 4.4 mmol), 5-(pyrid-2-yl)thien-2-yl-sulphonyl chloride (2.4 gm, 9 mmol), DMAP (0.5 gm), TEA (1.9 ml, 13 mmol) was stirred in dichloromethane (100 mL) for 5 hours. The solvent was removed under vacuum to yield a residue. Ethyl acetate (200 mL) was added to the residue. The solution was then washed with a saturated NaCl solution. The organic layer was dried over sodium sulfate and the solvent removed under vacuum to yield a crude oil. The crude oil was purified on a column (eluting with 5% MeOH/CH$_2$Cl$_2$) to yield the title compound as a solid.

$^1$H NMR (300 MHz, CDCl$_3$): δ1.23 (s, 3H), δ1.32 (s, 3H), δ1.39 (s, 3H), δ1.42 (s, 3H), δ3.68 (d, 1H, J=12.3 MHz), δ3.81 (d, 1H, J=12.3 MHz), δ4.10–4.25 (m, 4H), δ4.47(dd 1H, J=2.46 MHz, J=7.88 MHz), δ7.14 (t, 1H, J=7.2 MHz), δ7.36 (d, 1H, J=3.93 MHz), δ7.54 (d, 1H, J=7.71 MHz), δ7.59(d 1H J=7.71 MHz), δ7.67 (d, 1H, J=3.99 MHz), δ8.49(d 1H, J=4.6 MHz).

EXAMPLE 23

N-(benzyloxy-carbonyl)-2,3:4,5-bis-O-(1-methylethylidene)-β-D-fructopyranose sulfamate sodium salt

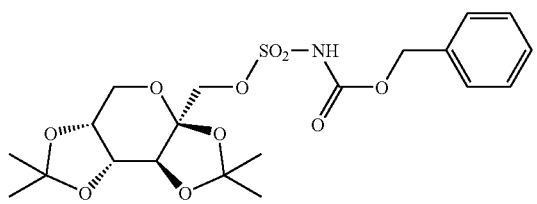

A 100 ml round bottom flask was charged with sodium hydride (0.1 g, 4 mmol) and THF (20 mL). The resulting suspension was slowly treated with a solution of N-(benzyloxy-carbonyl)-2,3:4,5-bis-O-(1-methylethylidene)-β-D-fructopyranose sulfamate (1.8 g, 4 mmol)(prepared as in Example 4) in THF (10 mL). After addition was complete the reaction was stirred for an additional 30 minutes. The solvent was concentrated under vacuum to yield a white solid, which was treated with with 95% ethanol (40 mL) to yield the title compound as a white solid.

M.P.>250° C. $^1$NMR (300 MHz, DMSO) δ 7.45–7.20 (5H, m), 4.86 (2H, s), 4.55 (1H, dd, J=8.1, 2.4 Hz), 4.38 (1H, d, J=2.8 Hz), 4.20 (1H, d, J=8.1 Hz), 3.84 (2H, q, J=28.2, 10.5 Hz), 3.73 (1H, d, J=13.3 Hz), 3.56 (1H, d, J=12.9 Hz), 1.44 (3H, s), 1.34 (3H, s), 1.33 (3H, s), 1.25 (3H, s)

Following the procedures described above, representative compounds of the instant invention were prepared, as listed in Table 1, 2 and 3. For compounds which were prepared as salts, the R1 is replaced with the salt cation.

TABLE 1

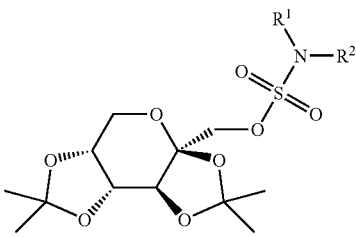

| Cmpd # | R$^1$ or salt cation | R$^2$ |
|---|---|---|
| 2 | H | —CH$_2$—CH=CH$_2$ |
| 3 | H | —CH$_2$—CH$_2$—Br |
| 4 | H | —CH$_2$—CH$_2$—CO$_2$—CH$_2$CH$_3$ |
| 5 | H | —CH$_2$—CO$_2$—CH$_3$ |
| 6 | H | Si(phenyl)$_3$ |
| 7 | H | —(CH$_2$)$_3$—CO$_2$H |
| 8 | H | —(CH$_2$)$_3$—CO$_2$—CH$_3$ |
| 9 | H | —OH |
| 10 | H | —OCH$_3$ |
| 11 | CH$_3$ | —OCH$_3$ |
| 12 | CH$_3$ | —OH |
| 13 | H | —C(O)O—Si(phenyl)$_3$ |
| 14 | H | —C(O)O-t-butyl |
| 15 | H | —C(O)O-benzyl |
| 16 | Na | —C(O)O-t-butyl |
| 17 | Na | —C(O)O-benzyl |
| 18 | Na | —C(O)—CH$_3$ |
| 19 | Na | —C(O)—CH$_2$CH$_3$ |
| 20 | Na | —SO$_2$—CF$_3$ |
| 21 | H | —CH$_2$—CH$_2$—N(CH$_3$)$_2$ |
| 22 | H | 3-pyrrolidinyl |
| 24 | H | benzyloxy |
| 26 | H | Benzyl |
| 27 | H | 4-methoxybenzyl |
| 28 | H | —C(O)—CH$_2$CH$_3$ |
| 29 | H | —C(O)—CH$_3$ |
| 30 | H | —SO$_2$—CF$_3$ |
| 31 | 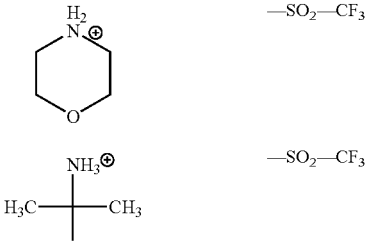 | —SO$_2$—CF$_3$ |
| 32 | NH$_3^⊕$ H$_3$C—C(CH$_3$)(CH$_3$)—CH$_3$ | —SO$_2$—CF$_3$ |
| 33 | SEM | SEM |

TABLE 1-continued

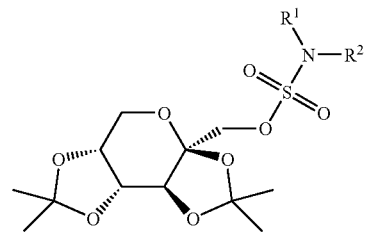

| Cmpd # | R¹ or salt cation | R² |
|---|---|---|
| 34 | H | —P(O)(C₆H₅)₂ |
| 35 | H | —(CH₂)₂—CO₂H |
| 36 | H | —CH₂—CO₂H |
| 37 | H | —CH—(C₆H₅)₂ |
| 40 | H | —C(O)-(2-methoxycarbonyl-phenyl) |
| 41 | H | —C(O)-(2-carboxy-phenyl) |
| 42 | H | —C(O)—(CH₂)₂—C(O)OCH₃ |
| 43 | H | —C(O)—(CH₂)₂—C(O)OH |
| 44 | H | —P(O)(OCH₂CH₃)₂ |
| 45 | —CH₂-phenyl | —CH₂-phenyl |
| 49 | H | —C(O)-(2-methoxyphenyl) |
| 50 | H | —C(O)-(3-methoxyphenyl) |
| 51 | H | —C(O)-n-propyl |
| 52 | H | —C(O)-benzyl |
| 53 | H | —C(O)-isobutyl |
| 54 | H | —C(O)—CH₂—OCH₃ |
| 55 | H | —C(O)-(2-tolyl) |
| 56 | H | —C(O)(3-tolyl) |
| 57 | H | —C(O)-(4-tolyl) |
| 58 | H | —C(O)-(4-methoxyphenyl) |
| 59 | H | —C(O)—CH₂—CH₂-phenyl |
| 60 | H | —C(O)—CH(ethyl)-n-butyl |
| 61 | H | —C(O)-phenyl |
| 62 | H | —SO₂-(4-trifluoromethoxy-phenyl) |
| 63 | H | —SO₂-(1-naphthyl) |
| 64 | H | —SO₂-(2-thienyl) |
| 65 | H | —SO₂-(4-trifluoromethyl-phenyl) |
| 66 | H | —SO₂-(2,6-difluoropehnyl) |
| 68 | H | —SO₂-(benzyl) |
| 69 | H | —SO₂-(4-methoxyphenyl) |
| 70 | H | —SO₂-(2-naphthyl) |
| 71 | H | —SO₂-(4-biphenyl) |
| 72 | H | —SO₂-(4,5-dibromo-2-thienyl) |
| 73 | H | —SO₂-(2-benzenesulfonyl-5-thienyl) |
| 74 | H | —SO₂—CF₃ |
| 75 | H | —SO₂-(2,2,2-trifluoroethyl) |
| 76 | H | —SO₂-phenyl |
| 77 | H | —SO₂-(2-chloro-1-ethyl) |
| 78 | H | —SO₂-isobutyl |
| 79 | H | —SO₂-(1-butyl) |
| 80 | H | —SO₂-(3-trifluoromethyl-phenyl) |
| 81 | H | —SO₂-(4-(2,1,3-benzoxadiazolyl)) |
| 82 | H | —SO₂-(4-(2-chloro-4-nitrophenoxy)-3,5-dichlorophenyl) |
| 83 | H | —SO₂-(4-bromophenyl) |
| 84 | H | —SO₂-ethyl |
| 85 | H | —SO₂-(8-quinolinyl) |
| 86 | H | —SO₂-(3,5-dimethyl-4-isoxazolyl) |
| 87 | H | —SO₂-(4-(2,1,3-benzothiadiazolyl)) |
| 88 | H | —SO₂-(1-propyl) |
| 89 | H | —SO₂-(4-acetamidophenyl) |
| 90 | H | —SO₂-(4-nitrophenyl) |
| 91 | H | —SO₂-(3-trifluoromethyl-phenyl) |
| 92 | ethyl | —C(O)—OCH₂CH₃ |
| 93 | H | —SO₂-(4-methylcarbonylamino-phenyl) |
| 95 | H | —SO₂-(2,4,6-trimethyl-phenyl) |
| 96 | H | —CH₂—CH₂—C(O)—OCH₃ |
| 98 | H | —SO₂-(2-(3-(2-pyridyl)-thienyl)) |

TABLE 1-continued

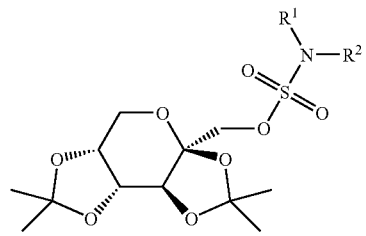

| Cmpd # | R¹ or salt cation | R² |
|---|---|---|
| 99 | H | —SO₂-(1-(5-dimethylamino-naphthyl)) |
| 100 | H | —SO₂—NH₂ |

TABLE 2

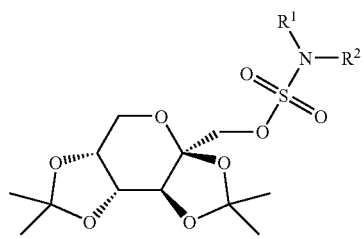

| Cmpd # | R¹ & R² taken together with the N atom |
|---|---|
| 38 | morpholinyl |
| 39 | 1-(2-isopropoxy-phenyl)-piperazinyl |
| 48 | isoindole-1,3-dione |

TABLE 3

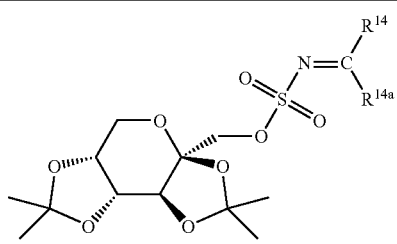

| Cmpd # | R¹⁴ | R¹⁴ᵃ |
|---|---|---|
| 46 | H | cyclohexyl |
| 47 | H | phenyl |
| 103 | H | dimethylamino |

| Cmpd # | R¹⁴ + R¹⁴ᵃ taken together |
|---|---|
| 102 | 2-(1-methyl-pyrrolidinyl) |

Molecular weights for representative compounds listed in Tables 1, 2 and 3 were measured on an Agilent 1100 HPLC/MSD Mass Spectrometer, with results as listed in Table 4.

TABLE 4

| Cmpd # | Ion Measured | Calc'd MW | Meas MW |
|---|---|---|---|
| 2 | [M + Na]⁺ | 402.12 | 402 |
| 3 | [M + Na]⁺ | 468.03 | 468 |
| 4 | [M − H]⁻ | 438.14 | 438 |

TABLE 4-continued

| Cmpd # | Ion Measured | Calc'd MW | Meas MW |
|---|---|---|---|
| 5 | [M + Na]+ | 434.11 | 434 |
| 7 | [M + H]+ | 426.14 | 426 |
| 8 | [M − H]− | 438.14 | 438 |
| 9 | [M − H]− | 356.1 | 356 |
| 10 | [M + Na]+ | 392.1 | 392 |
| 11 | [M + Na]+ | 406.11 | 406 |
| 14 | [M − H]− | 438.14 | 438 |
| 15 | [M − H]− | 472.13 | 472 |
| 21 | [M − H]+ | 411.18 | 411 |
| 24 | [M + H]+ | 446.15 | 446 |
| 27 | [M + Na]+ | 482.15 | 482 |
| 28 | [M + H]+ | 396.13 | 396 |
| 29 | [M − H]− | 380.1 | 380 |
| 33 | [M + Na]+ | 622.25 | 622 |
| 34 | [M + H]+ | 540.15 | 540 |
| 37 | [M + Na]+ | 528.17 | 528 |
| 38 | [M + H]+ | 410.15 | 410 |
| 39 | [M + H]+ | 543.24 | 543 |
| 40 | [M + Na]+ | 524.12 | 524 |
| 41 | [M − H]− | 486.11 | 486 |
| 42 | [M + H]+ | 454.14 | 454 |
| 43 | [M − H]− | 438.11 | 438 |
| 44 | [M − H]− | 474.12 | 474 |
| 45 | [M + H]+ | 520.2 | 520 |
| 47 | [M + H]+ | 428.14 | 428 |
| 48 | [M + Na]+ | 492.09 | 492 |
| 49 | [M + H]+ | 473.5 | 474 |
| 50 | [M + H]+ | 473.5 | 474 |
| 51 | [M + H]+ | 409.5 | 410 |
| 52 | [M + H]+ | 457.1 | 457 |
| 53 | [M + H]+ | 423.5 | 424 |
| 54 | [M + H]+ | 411.4 | 412 |
| 55 | [M + H]+ | 457.5 | 458 |
| 56 | [M + H]+ | 457.5 | 458 |
| 57 | [M + H]+ | 457.5 | 458 |
| 58 | [M + H]+ | 473.5 | 474 |
| 92 | [M + H]+ | 478.3 | 478 |
| 101 | [M − H]− | 573.6 | 573.1 |

EXAMPLE 24 & 25

In Vivo Testing, Maximal Electoshock Seizure

Anticonvulsant activity was determined using the standard MES model for generalized tonic-clonic seizures (Swinyard E A, Woodhead J H, White H S, Franklin M R, In: Levy R H, Mattson R H, Meldrum B S, Penry J K, Dreifuss F E eds. *Antiepileptic drugs*. New York: Raven Press, 1989:85–102).

An electric stimulus of 0.2 sec duration, 60 Hz, 50 mA in mice, 150 mA in rats, was delivered via corneal electrodes primed with an electrolyte solution containing an anesthetic agent (0.5% tetracaine hydrochloride in 0.9% saline).

Mice or rats were randomly selected into control and test groups. The animals were dosed with vehicle or test compound, at varying concentrations. Mice were subjected to the electrical stimulus at 30 minutes and 4 hours following administration of test compound. Rats were subjected to electrical stimulus at time intervals between 15 minutes and 4 hours following administration of test compound. Abolition of the hind limb tonic extensor component was an indication of the test compound's ability to inhibit MES-induced seizure spread.

The $ED_{50}$ (the calculated dose required to block the hindlimb tonic-extensor component of the maximal electroshock seizure in 50% of the animals tested) was calculated. A probit analysis (Finney D J. Probit Analysis. Cambridge, England: Cambridge University Press, 1971) was used to calculate the $ED_{50}$.

Following the mouse procedure described above, representative compounds of the instant invention were tested for biological activity in the mouse, with results as listed in Table 5. Mouse activity is listed as number of mice active/total number of mice tested @ time after administration of the test compound.

TABLE 5

| Cmpd # | Mouse Activity | Dosage (mg/kg) |
|---|---|---|
| 3 | No Activity | 30, 100, 300 |
| 4 | No Activity | 30, 100, 300 |
| 5 | No activity | 30, 100, 300 |
| 6 | No activity | 30, 100, 300 |
| 8 | No activity | 30, 100 |
| 8 | 1/1 @ 0.5 hrs | 300 |
| 9 | No activity | 30 |
| 9 | 1/1 @ 4 hrs | 300 |
| 10 | No activity | 30, 100 |
| 10 | 1/1 @ 0.5 hrs | 300 |
|  | 1/1 @ 4 hrs |  |
| 11 | No activity | 30, 100, 300 |
| 12 | No activity | 30, 100, 300 |
| 13 | No activity | 30, 100, 300 |
| 14 | No activity | 30, 100, 300 |
| 15 | No activity | 30 |
| 15 | 3/3 @ 1 hr | 100 |
|  | 2/3 @ 4 hrs |  |
| 15 | 1/1 @ 0.5 hrs | 300 |
|  | 1/1 @ 4 hrs |  |
| 18 | No activity | 30 |
| 18 | 1/3 @ 0.5 hrs | 100 |
|  | 2/3 @ 4 hrs |  |
| 18 | 1/1 @ 0.5 hrs | 300 |
|  | 1/1 @ 4 hrs |  |
| 19 | No activity | 30 |
| 19 | 0/3 @ 0.5 hrs | 100 |
|  | 3/3 @ 4 hrs |  |
| 19 | 1/1 @ 0.5 hrs | 300 |
|  | 1/1 @ 4 hrs |  |
| 30 | No activity | 30 |
| 30 | 2/3 @ 0.5 hrs | 100 |
|  | 3/3 @ 4 hrs |  |
| 30 | 1/1 @ 0.5 hrs | 300 |
|  | 1/1 @ 4 hrs |  |
| 35 | No Activity | 30, 100 |
| 35 | 1/1 @ 0.5 hrs | 300 |
| 37 | No Activity | 30 |
| 37 | 1/3 @ ¼ hrs, 2 hrs, 6 hrs | 100 |
| 37 | 0/3 @ ½ hr, 1 hr | 100 |
| 37 | No activity | 300 |
| 39 | No activity | 30, 100, 300 |
| TPM | @ 2 hrs | ED50 = 33 m/k |

Following the rat procedure described above, representative compounds of the instant invention were tested for biological activity in the rat, with results as listed in Table 6 and 7. Rat activity is listed as number of rats active/total number of rats tested @ time after administration of the test compound.

TABLE 6

| Cmpd # | Rat Activity (oral) | Dosage (mg/kg) |
|---|---|---|
| 2 | 3/4 @ 2 hrs | 8 |
|  | 2/4 @ 4 hrs |  |
|  | 1/4 @ 6 hrs |  |
|  | 1/4 @ 8 hrs |  |

TABLE 6-continued

| Cmpd # | Rat Activity (oral) | Dosage (mg/kg) |
|---|---|---|
| 2 | 1/4 @ 0.5 hrs<br>2/2 @ 2 hrs<br>1/2 @ 4 hrs<br>1/2 @ 6 hrs | 20 |
| 2 | 3/8 @ 1 hr<br>4/8 @ 2 hrs<br>2/8 @ 4 hrs<br>1/8 @ 6 hrs | 200 |
| 3 | 1/4 @ 1 hr<br>2/4 @ 2 hrs | 30 |
| 4 | 1/4 @ 1 hr | 30 |
| 5 | 3/4 @ 2 hrs<br>1/4 @ 4 hrs | 30 |
| 9 | 1/4 @ 1 hr<br>1/4 @ 4 hrs<br>2/4 @ 2 hrs | 30 |
| 11 | 2/3 @ 0.5 hrs<br>2/3 @ 2 hrs<br>2/3 @ 4 hrs | 30 |
| 12 | 1/4 @ 1 hr | 15 |
| 13 | 1/4 @ 0.5 hrs<br>1/4 @ 1 hr | 30 |
| 14 | 3/4 @ 2 hrs<br>4/4 @ 4 hrs | 30 |
| 17 | 1/4 @ 0.25 hrs<br>2/4 @ 0.5 hrs<br>1/4 @ 1 hr<br>4/4 @ 2 hrs<br>4/4 @ 4 hrs | 30 |
| 18 | 1/4 @ 0.25 hrs<br>1/4 @ 0.5 hrs<br>1/4 @ 2 hrs<br>3/4 @ 4 hrs | 30 |
| 19 | 1/4 @ 0.25 hrs<br>0/4 @ 0.5 hrs<br>1/4 @ 1 hr<br>4/4 @ 2 hrs<br>4/4 @ 4 hrs | 30 |
| 30 | 3/4 @ 0.25 hrs<br>4/4 @ 0.5 hrs<br>3/4 @ 1 hr<br>4/4 @ 2 hrs<br>4/4 @ 4 hrs | 30 |
| 37 | 1/4 @ 1 hr<br>2/4 @ 2 hrs<br>1/4 @ 4 hrs | 30 |
| 39 | 1/4 @ 4 hrs | 30 |

TABLE 7

| Cmpd # | $ED_{50}$ (m/k) |
|---|---|
| 2 | 11.89 @ 2 hrs |
| 5 | >80 @ 2 hrs |
| 9 | 68.72 @ 4 hrs |
| 11 | 26.75 @ 4 hrs |
| 17 | 10.37 @ 4 hrs,<br>3.26 @ 6 hrs |
| 19 | 11.22 @ 4 hrs |
| 30 | 2.38 @ 4 hrs |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of the formula (I)

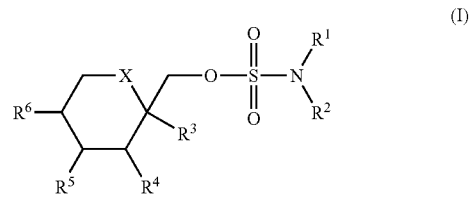

(I)

wherein
X is O;
$R^1$ is selected from the group consisting of hydrogen, alkyl, alkenyl, alkynyl, cycloalkyl, cycloalkyl-alkyl, cycloalkenyl, aryl, aralkyl, heteroaryl, heteroaryl-alkyl, heterocycloalkyl, heterocycloalkyl-alkyl, alkoxycarbonylalkyl, —($C_{2-8}$alkyl)-O—C(O)-(alkyl), —C(O)—$R^9$, —C(O)-(alkyl)-O-(alkyl), alkoxycarbonyl, aryloxycarbonyl, aralkyloxycarbonyl, —Si($R^{10}$)($O_{0-1}R^{11}$)$_2$, —$SO_2R^{12}$ and 2-(trimethylsilyl)ethoxmetyl;
wherein the alkyl, cycloalkyl, aryl, heteroaryl or heterocycloalkyl group, whether alone or as part of the $R^1$ substituent group, is optionally substituted with one or more substituents independently selected from halogen, hydroxy, carboxy, alkyl, alkoxy, aryl, aralkyl, amino, alkylamino, dialkylamino, nitro or cyano;
$R^2$ is selected from the group consisting of hydroxy, alkyl, alkoxy, alkenyl, alkynyl, cycloalkyl, cycloalkyl-alkyl, cycloalkenyl, aryl, aryloxy, aralkyl, aralkyloxy, heteroaryl, heteroaryl-alkyl, heterocycloalkyl, heterocycloalkylalkyl, alkoxycarbonylalkyl, —($C_{2-8}$alkyl)-O—C(O)-(alkyl), —C(O)—$R^9$, —C(O)-(alkyl)-O-(alkyl), alkoxycarbonyl, aryloxycarbonyl, aralkyloxycarbonyl, —C(O)O—Si($R^{17}$)$_3$, —Si($R^{10}$)($O_{0-1}R^{11}$)$_2$, —$SO_2R^{12}$, —P(=O)($R_{13}$)$_2$ and 2-(trimethylsilyl)ethoxmetyl;
wherein the alkyl, cycloalkyl, aryl, aralkyl, heteroaryl or heterocycloalkyl group, whether alone or as part of the $R^2$ substituent group, is optionally substituted with one or more substituents independently selected from halogen, hydroxy, carboxy, alkyl, alkoxy, aryl, aralkyl, amino, alkylamino, dialkylamino, nitro or cyano;
wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;
wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;
wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;
wherein each $R^{12}$ is independently selected from amino, alkylamino, dialkylamino, alkyl, aryl, aralkyl or heteroaryl; wherein the alkyl, aryl or heteroaryl groups, whether alone or as part of an $R^{12}$ substituent group, is optionally substituted with one or more substituents independently selected from alkyl, halogen, trifluoromethyl, trifluoromethoxy, alkyl, alkoxy, nitro, amino, alkylamino, dialkylamino, alkylcarbonylamino, arylcarbonylamino, aralkylcarbonylamino, aryl, heteroaryl, benzenesulfonyl or phenoxy; wherein the phenoxy group is optionally substituted with one or more substituents independently selected from halogen, alkyl, alkoxy or nitro;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively, $R^1$ and $R^2$ are taken together with the N atom to which they are bound to form a heteroaryl or heterocycloalkyl group; wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH)alkylamino or —C(=NH)-dialkylamino; wherein the aryl substituent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH)-amino, —C(=NH)-alkylamino or —C(=NH)-dialkylamino group is bound to the aryl, heteroaryl or heterocycloalkyl;

alternatively $R^1$ and $R^2$ are taken together with the nitrogen atom to which they are bound to form —N=C$(R^{14})_2$;

wherein each $R^{14}$ is independently selected from hydrogen, alkyl, cycloalkyl, dialkylamino, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

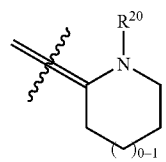

wherein $R^{20}$ is lower alkyl;

$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

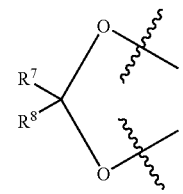

wherein $R^7$ and $R^8$ are the same or different and are hydrogen, lower alkyl or are alkyl and are joined to form a cyclopentyl or cyclohexyl ring;

provided that when $R^1$ is alkyl, $R^2$ is other than alkyl;

provided further that when $R^1$ is hydrogen, $R^2$ is other than alkyl, methylcarbonyl, phenyl, benzyl or carboxyalkyl;

provided further that $R^1$ and $R^2$ when taken together with the nitrogen atom to which they are bound is other than imidazolyl;

provided further that when X is O, $R^3$ and $R^4$ are taken together to form a methylenedioxy group of the formula:

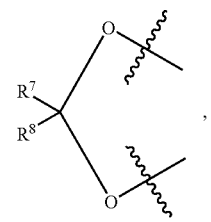

$R^5$ and $R^6$ are taken together to form a methylenedioxy group of the formula:

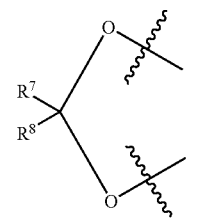

wherein $R^7$ and $R^8$ in each instance are each methyl, and $R^1$ is hydrogen then $R^2$ is other than isopropylsulfonyl, 4-(N-benzyl)-piperidinyl or 4-pyridyl;

or a pharmaceutically acceptable salt thereof.

2. A compound as in claim 1 of the formula (It)

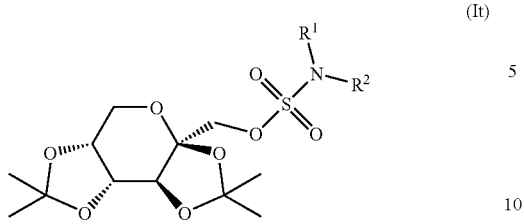

(It)

wherein
R¹ is selected from the group consisting of hydrogen, alkyl, alkenyl, alkynyl, cycloalkyl, cycloalkyl-alkyl, cycloalkenyl, aryl, aralkyl, heteroaryl, heteroaryl-alkyl, heterocycloalkyl, heterocycloalkyl-alkyl, alkoxycarbonylalkyl, —($C_{2-8}$alkyl)-O—C(O)-(alkyl), —C(O)—R⁹, —C(O)-(alkyl)-O-(alkyl), alkoxycarbonyl, aryloxycarbonyl, aralkyloxycarbonyl, —Si(R¹⁰)($O_{0-1}$R¹¹)₂, —SO₂R¹² and 2-(trimethylsilyl)ethoxmetyl;
wherein the alkyl, cycloalkyl, aryl, heteroaryl or heterocycloalkyl group, whether alone or as part of the R¹ substituent group, is optionally substituted with one or more substituents independently selected from halogen, hydroxy, carboxy, alkyl, alkoxy, aryl, aralkyl, amino, alkylamino, dialkylamino, nitro or cyano;
R² is selected from the group consisting of hydroxy, alkyl, alkoxy, alkenyl, alkynyl, cycloalkyl, cycloalkyl-alkyl, cycloalkenyl, aryl, aryloxy, aralkyl, aralkyloxy, heteroaryl, heteroaryl-alkyl, heterocycloalkyl, heterocycloalkylalkyl, alkoxycarbonylalkyl, —($C_{2-8}$alkyl)-O—C(O)-(alkyl), —C(O)—R⁹, —C(O)-(alkyl)-O-(alkyl), alkoxycarbonyl, aryloxycarbonyl, aralkyloxycarbonyl, —C(O)O—Si(R¹⁷)₃, —Si(R¹⁰)($O_{0-1}$R¹¹)₂, —SO₂R¹², —P(=O)(R¹³)₂ and 2-(trimethylsilyl)ethoxmetyl;
wherein the alkyl, cycloalkyl, aryl, aralkyl, heteroaryl or heterocycloalkyl group, whether alone or as part of the R² substituent group, is optionally substituted with one or more substituents independently selected from halogen, hydroxy, carboxy, alkyl, alkoxy, aryl, aralkyl, amino, alkylamino, dialkylamino, nitro or cyano;
wherein each R⁹ is independently selected from alkyl, aryl, aralkyl or heteroaryl; wherein the alkyl, aryl or heteroaryl group, whether alone or as part of an R⁹ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;
wherein each R¹⁰ is independently selected from hydrogen, alkyl, aryl or aralkyl; wherein the alkyl or aryl group, whether alone or as part of an R¹⁰ substituent group, is optionally substituted with one or more substituents independently selected from halogen, hydroxy, carboxy, alkyl, alkoxy, aryl, aralkyl, amino, alkylamino, dialkylamino, nitro or cyano;
wherein each R¹¹ is independently selected from alkyl, aryl or aralkyl; wherein the alkyl or aryl group, whether alone or as part of an R¹¹ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;
wherein each R¹² is independently selected from amino, alkylamino, dialkylamino, alkyl, aryl, aralkyl or heteroaryl; wherein the alkyl, aryl or heteroaryl groups, whether alone or as part of an R¹² substituent group, is optionally substituted with one or more substituents independently selected from alkyl, halogen, trifluoromethyl, trifluoromethoxy, alkyl, alkoxy, nitro, amino, alkylamino, dialkylamino, alkylcarbonylamino, arylcarbonylamino, aralkylcarbonylamino, aryl, heteroaryl, benzenesulfonyl or phenoxy; wherein the phenoxy group is optionally substituted with one or more substituents independently selected from halogen, alkyl, alkoxy or nitro;
wherein each R¹³ is independently selected from alkyl, alkoxy, aryl, aryloxy, aralkyl or aralkyloxy; wherein the alkyl or aryl group, whether alone or as part of an R¹³ substituent group, is optionally substituted with one or more substituents independently selected from halogen, hydroxy, carboxy, alkyl, alkoxy, aryl, aralkyl, amino, alkylamino, dialkylamino, nitro or cyano;
wherein each R¹⁷ is independently selected from alkyl, aryl or aralkyl; wherein the alkyl or aryl group, whether alone or as part of an R¹⁷ substituent group, is optionally substituted with one or more substituents independently selected from halogen, hydroxy, carboxy, alkyl, alkoxy, aryl, aralkyl, amino, alkylamino, dialkylamino, nitro or cyano;
alternatively, R¹ and R² are taken together with the N atom to which they are bound to form a heteroaryl or heterocycloalkyl group; wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH)alkylamino or —C(=NH)-dialkylamino; wherein the aryl substituent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH)-amino, —C(=NH)-alkylamino or —C(=NH)-dialkylamino group is bound to the aryl, heteroaryl or heterocycloalkyl;
alternatively R¹ and R² are taken together with the nitrogen atom to which they are bound to form —N=C(R¹⁴)₂;
wherein each R¹⁴ is independently selected from hydrogen, alkyl, cycloalkyl, dialkylamino, aryl or aralkyl; wherein the alkyl, cycloalkyl or aryl group, whether alone or as part of an R¹⁴ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one R¹⁴ is selected from the group consisting of hydrogen and alkyl;
alternatively, two R¹⁴ groups are taken together with the carbon atom to which they are bound to form a heterocycloalkyl group of the formula

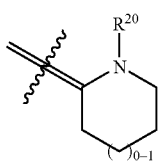

wherein $R^{20}$ is lower alkyl;

provided that when $R^1$ is alkyl, $R^2$ is other than alkyl;

provided further that when $R^1$ is hydrogen, $R^2$ is other than alkyl, methylcarbonyl, phenyl, benzyl or carboxyalkyl;

provided further that $R^1$ and $R^2$ when taken together with the nitrogen atom to which they are bound is other than imidazolyl;

provided further that when $R^1$ is hydrogen then $R^2$ is other than isopropylsulfonyl, 4-(N-benzyl)-piperidinyl or 4-pyridyl;

or a pharmaceutically acceptable salt thereof.

3. A compound as in claim 1 wherein $R^1$ is selected from the group consisting of hydrogen, lower alkyl and aralkyl;

$R^2$ is selected from the group consisting of hydroxy, alkyl, benzhydryl, alkoxy, alkenyl, aryl, aralkyl, aralkyloxy, alkoxycarbonylalkyl, —C(O)—$R^9$, alkoxycarbonyl, aralkyloxycarbonyl, —C(O)-(alkyl)-O-(alkyl), a nitrogen containing heteroaryl, a nitrogen containing heterocycloalkyl, —SO$_2$R$^{12}$, —C(O)O—Si(R$^{17}$)$_3$, —Si(R$^{10}$)(O$_{0-1}$R$^{11}$)$_2$, —P(=O)(R$^{13}$)$_2$ and 2-(trimethylsilyl)ethoxymethyl;

wherein the alkyl, aralkyl, nitrogen containing heteroaryl or nitrogen containing heterocycloalkyl, whether alone or as part of a substituent group, is optionally substituted with one or more substituents independently selected from halogen, hydroxy, carboxy, alkyl, alkoxy, aryl, aralkyl, amino, alkylamino, dialkylamino, nitro or cyano;

provided that when $R^1$ is lower alkyl, $R^2$ is other than alkyl;

provided further that when $R^1$ is hydrogen, $R^2$ is other than alkyl, methylcarbonyl, phenyl, benzyl or carboxyalkyl;

provided further that when $R^1$ is hydrogen then $R^2$ is other than isopropylsulfonyl, 4-(N-benzyl)-piperidinyl or 4-pyridyl;

or a pharmaceutically acceptable salt thereof.

4. A compound as in claim 3 wherein $R^2$ is selected from the group consisting of —C(O)—$R^9$, —C(O)-(alkyl)-O-(alkyl) and —SO$_2$R$^{12}$.

5. A compound as in claim 1 wherein $R^1$ and $R^2$ are taken together with the nitrogen atom to which they are bound to form a group selected from heteroaryl or heterocycloalkyl;

wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH)alkylamino or —C(=NH)-dialkylamino; wherein the aryl substituent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH)-amino, —C(=NH)-alkylamino or —C(=NH)-dialkylamino group is bound to the aryl, heteroaryl or heterocycloalkyl;

provided that $R^1$ and $R^2$ when taken together with the nitrogen atom to which they are bound is other than imidazolyl;

or a pharmaceutically acceptable salt thereof.

6. A compound as in claim 5 wherein $R^1$ and $R^2$ are taken together with the N atom to which they are bound to form a group selected from morpholinyl or 1-(2-isopropoxyphenyl)-piperazinyl, isoindole-1,3-dione; or a pharmaceutically acceptable salt thereof.

7. A compound as in claim 3 wherein $R^1$ and $R^2$ are taken together with the nitrogen atom to which they are bound to form —N=C(R$^{14}$)$_2$;

wherein $R^{14}$ is selected from the group consisting of hydrogen, dialkylamino, cycloalkyl and aryl; wherein the cycloalkyl or aryl is optionally substituted with one or more substituents independently selected from halogen, hydroxy, carboxy, alkyl, alkoxy, aryl, aralkyl, amino, alkylamino, dialkylamino, nitro or cyano;

alternatively, two $R^{14}$ groups are taken together with the carbon atom to which they are bound to form a heterocycloalkyl group of the formula

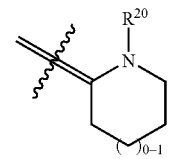

wherein $R^{20}$ is lower alkyl;

or a pharmaceutically acceptable salt thereof.

8. A compound as in claim 7 wherein $R^{14}$ is selected from the group consisting of hydrogen, di(lower alkyl)amino, aryl and cycloalkyl; or a pharmaceutically acceptable salt thereof.

9. A compound as in claim 8, wherein $R^{14}$ is selected from the group consisting of dimethylamino, cyclohexyl and phenyl; or a pharmaceutically acceptable salt thereof.

10. A compound as in claim 7, wherein two $R^{14}$ group are taken together with the carbon atom to which they are bound to form 2-(1-methyl-pyrrolidinyl).

11. A compound as in claim 3 wherein $R^1$ is selected from the group consisting of hydrogen, alkyl, aralkyl and 2-(trimethylsilyl)ethoxymethyl;

$R^2$ is selected from the group consisting of hydroxy, halogenated alkyl, benzhydryl, alkoxy, alkenyl, aralkyl (wherein the aralkyl is optionally substituted with a substituent selected from alkoxy), aralkyloxy, alkoxycarbonylalkyl, carboxyalkyl, alkylcarbonyl (wherein the alkyl is optionally substituted with a substituent selected from carboxy or alkoxycarbonyl), arylcarbonyl (wherein the aryl is optionally substituted with a substituent selected from alkyl, alkoxy, alkoxycarbonyl or carboxy), aralkycarbonyl, alkoxycarbonyl, aralkyloxycarbonyl, alkoxyalkylcarbonyl, aminoalkyl, alkylaminoalkyl, dialkylaminoalkyl, a nitrogen containing heteroaryl, a nitrogen containing heterocycloalkyl, aminosulfonyl (wherein the amino group is optionally substituted with one to two lower alkyl), alkylsulfonyl (wherein the alkyl group is optionally substituted with one to three substituents independently selected from halogen), arylsulfonyl (wherein the aryl group is optionally substituted with one to three substituents independently selected from alkyl, trifluoromethyl, trifluoromethoxy, halogen, alkoxy, alkylcarbonylamino, acetamido, nitro, amino, alkylamino, dialkylamino or 2-chloro-4-nitrophenyoxy), aralkylsulfonyl, biphenylsulfonyl, heteroarylsulfonyl (wherein the heteroaryl is optionally substituted with one to two substituents independently selected from halogen, alkyl, heteroaryl or benzenesulfonyl), benzhydryl, —Si—(aryl)$_3$, —C(O)O—Si(aryl)$_3$, —P(=O)(aryl)$_2$, —P(=O)(alkoxy)$_2$ and 2-(trimethylsilyl)ethoxymethyl;

provided that when $R^1$ is hydrogen, then $R^2$ is other than methylcarbonyl, phenyl, benzyl or carboxyalkyl;

provided further that when $R^1$ is hydrogen, $R^2$ is other than isopropylsulfonyl or 4-pyridyl;

or a pharmaceutically acceptable salt thereof.

12. A compound as in claim 11 wherein
$R^1$ is selected from the group consisting of hydrogen, methyl, ethyl, benzyl and 2-(trimethylsilyl)ethoxymethyl;
$R^2$ is selected from the group consisting of hydroxy, methoxy, allyl, 1-(2-bromo)-ethyl, 1-(2-ethoxycarbonyl)ethyl, methoxycarbonylmethyl, methoxycarbonylethyl, 1-(methoxycarbonyl)-n-propyl, carboxymethyl, 1-(3-carboxy)-n-propyl, 1-(2-carboxy)ethyl, ethoxycarbonyl, t-butoxycarbonyl, benzyloxycarbonyl, methylcarbonyl, ethylcarbonyl, n-propylcarbonyl, isobutylcarbonyl, phenylethylcarbonyl, benzylcarbonyl, phenylcarbonyl, 2-methoxycarbonylphenyl-carbonyl, 2-carboxyphenyl-carbonyl, methoxycarbonyl-ethylcarbonyl, carboxyethylcarbonyl, diethoxy-phosphinyl, triphenylsilyl, triphenylsilyloxycarbonyl, trifluoromethylsulfonyl, dimethylaminoethyl, benzyl, 4-methoxybenzyl, benzyloxy, 3-pyrrolidinyl, 4-pyridyl, 4-(N-benzyl)-piperidinyl, 2-(trimethylsilyl)ethoxymethyl, diphenylphosphinyl, benzhydryl, 2-methoxyphenylcarbonyl, 3-methoxyphenylcarbonyl, 4-methoxyphenylcarbonyl, methoxymethylcarbonyl, 2-tolylcarbonyl, 3-tolylcarbonyl, 4-tolylcarbonyl, 5-heptylcarbonyl, aminosulfonyl, 4-trifluoromethoxyphenylsulfonyl, 1-naphthylsulfonyl, 2-naphthylsulfonyl, 1-(5-dimethylamino)-naphthyl-sulfonyl, 4-biphenylsulfonyl, 2-thienylsulfonyl, 2-(3-(2-pyridyl)-thienyl)-sulfonyl, 4-trifluoromethylphenylsulfonyl, 3-trifluoromethylphenylsulfonyl, 2,6-difluorophenylsulfonyl, benzylsulfonyl, 4-methoxyphenylsulfonyl, 4,5-dibromo-2-thienylsulfonyl, 2-benzenesulfonyl-5-thienylsulfonyl, trifluoromethylsulfonyl, 3-trifluoromethylphenylsulfonyl, 2,2,2-trifluoroethylsulfonyl, phenylsulfonyl, 2,4,6-trimethylphenyl-sulfonyl, 2-chloro-1-ethylsulfonyl, isopropylsulfonyl, isobutylsulfonyl, 1-butylsulfonyl, 4-(2,1,3,-benzoxadiazolyl)sulfonyl, 4-(2-chloro-4-nitrophenoxy)-3,5-dichlorophenylsulfonyl, 4-bromophenylsulfonyl, ethylsulfonyl, 8-quinolinylsulfonyl, 3,5-dimethyl-4-isoxazolylsulfonyl, 4-(2,1,3-benzothidiazolyl)sulfonyl, 1-propylsulfonyl, 4-methylcarbonylaminophenyl-sulfonyl, 4-acetamidophenylsulfonyl and 4-nitrophenylsulfonyl;

provided that when $R^1$ is hydrogen, then $R^2$ is other than methylcarbonyl, phenyl, benzyl or carboxymethyl;

provided further that when $R^1$ is hydrogen, $R^2$ is other than isopropylsulfonyl 4-(N-benzyl)-piperidinyl or 4-pyridyl;

or a pharmaceutically acceptable salt thereof.

13. A compound as in claim 12 wherein
$R^1$ is selected from the group consisting of hydrogen and methyl;
$R^2$ is selected from the group consisting of hydroxy, methoxy, allyl, 1-(3-methoxycarbonyl)-n-propyl, 1-(2-carboxy)ethyl, 1-(2-bromo)-ethyl, 1-(2-ethoxycarbonyl)ethyl, methoxycarbonylmethyl, t-butoxycarbonyl, benzyloxycarbonyl, methylcarbonyl, ethylcarbonyl, triphenylsilyl, triphenylsilyloxycarbonyl, trifluoromethylsulfonyl and benzhydryl;
alternatively $R^1$ and $R^2$ are taken together with the nitrogen atom to which they are bound to form 1-(2-isopropoxyphenyl)-piperidinyl;
provided that when $R^1$ is hydrogen, then $R^2$ is other than methylcarbonyl;
or a pharmaceutically acceptable salt thereof.

14. A pharmaceutical composition comprising a pharmaceutically acceptable carrier and a compound of claim 1.

15. A pharmaceutical composition made by mixing a compound of claim 1 and a pharmaceutically acceptable carrier.

16. A process for making a pharmaceutical composition comprising mixing a compound of claim 1 and a pharmaceutically acceptable carrier.

17. A method of treating epilepsy, in a subject in need thereof comprising administering to the subject a therapeutically effective amount of the compound of claim 1.

18. A process for the preparation of a compound of formula (XX)

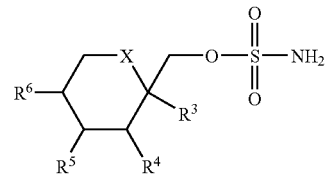

(XX)

wherein
X is O;
$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

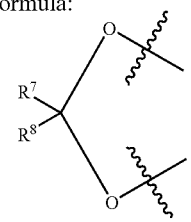

wherein $R^7$ and $R^8$ are same or different and are hydrogen, lower alkyl or are alkyl and are joined to form a cyclopentyl or cyclohexyl ring;

comprising, reacting a compound of formula (Ij)

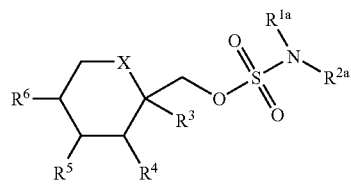

(Ij)

wherein
X is O;

$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —Si$(R^{10})(O_{0-1}R^{11})_2$, and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{1a}$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si$(R^{17})_3$, —Si$(R^{10})(O_{0-1}R^{11})_2$, —P(=O)$(R^{13})_2$ and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{2a}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

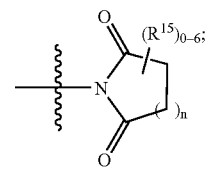

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C$(R^{14})_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

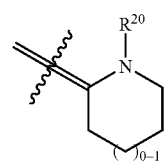

wherein $R^{20}$ is lower alkyl;

$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

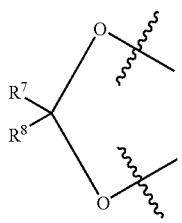

wherein R$^7$ and R$^8$ are same or different and are hydrogen, lower alkyl or are alkyl and are joined to form a cyclopentyl or cyclohexyl ring;

or a pharmaceutically acceptable salt thereof;

under de-protection conditions to yield the compound of formula (XX).

19. The process as in claim 18, wherein the de-protection conditions are catalytic reduction.

20. The process as in claim 18, wherein the de-protection conditions are acid cleavage.

21. The process as in claim 18, wherein the de-protection conditions are basic cleavage.

22. The process as in claim 18, wherein the compound of formula (Ij) is reacted with hydrazine, methylhydrazine or phenylhydrazine.

23. A process as in claim 18, wherein the compound of formula (XX) is a compound of formula (XXa)

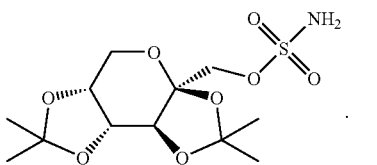
(XXa)

24. A process for the preparation of a compound of formula (XXa)

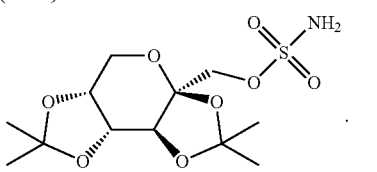
(XXa)

comprising reacting a compound of formula (Ik)

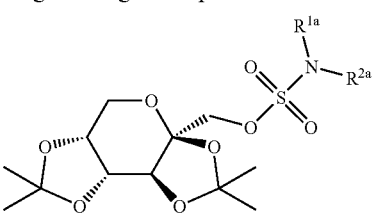
(Ik)

wherein

R$^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-C$_1$alkyl, heterocycloalkyl-C$_1$alkyl, alkoxycarbonylC$_2$alkyl, —C(O)—R$^9$, —C(O)-(alkyl)-O-(alkyl), alkoxycarbonyl, aryloxycarbonyl, benzyloxycarbonyl, —Si(R$^{10}$)(O$_{0-1}$R$^{11}$)$_2$, and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the R$^{1a}$ substituent group, is optionally substituted with one or more substituents independently selected from halogen, hydroxy, carboxy, alkyl, alkoxy, aryl, aralkyl, amino, alkylamino, dialkylamino, nitro or cyano;

R$^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-C$_1$alkyl, heterocycloalkyl-C$_1$alkyl, alkoxycarbonylC$_2$alkyl, —C(O)—R$^9$, —C(O)-(alkyl)-O-(alkyl), alkoxycarbonyl, aryloxycarbonyl, benzyloxycarbonyl, —C(O)O—Si(R$^{17}$)$_3$, —Si(R$^{10}$)(O$_{0-1}$R$^{11}$)$_2$, —P(=O)(R$^{13}$)$_2$ and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the R$^{2a}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^9$ is independently selected from alkyl, aryl, aralkyl or heteroaryl; wherein the alkyl, aryl or heteroaryl group, whether alone or as part of an R$^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each R$^{10}$ is independently selected from hydrogen, alkyl, aryl or aralkyl; wherein the alkyl or aryl group, whether alone or as part of an R$^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^{11}$ is independently selected from alkyl, aryl or aralkyl; wherein the alkyl or aryl group, whether alone or as part of an R$^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each R$^{13}$ is independently selected from alkyl, alkoxy, aryl, aryloxy, aralkyl or aralkyloxy; wherein the alkyl or aryl group, whether alone or as part of an R$^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each R$^{17}$ is independently selected from alkyl, aryl or aralkyl; wherein the alkyl or aryl group, whether alone or as part of an R$^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

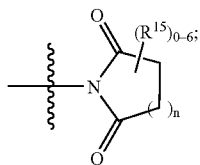

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C($R^{14}$)$_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

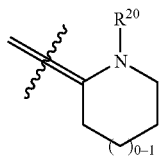

wherein $R^{20}$ is lower alkyl;
or a pharmaceutically acceptable salt thereof;
under de-protection conditions to yield the compound of formula (XXa).

25. The process as in claim 24, wherein the de-protection conditions are catalytic reduction.

26. The process as in claim 24, wherein the de-protection conditions are acid cleavage.

27. The process as in claim 24, wherein the de-protection conditions are basic cleavage.

28. The process as in claim 24, wherein the compound of formula (Ik) is reacted with hydrazine, methylhydrazine or phneylhydrazine.

29. A compound as in claim 1 of the formula (Ij)

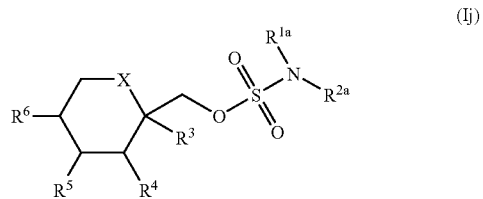

wherein
X is O;
$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-C$_1$alkyl, heterocycloalkyl-C$_1$alkyl, alkoxycarbonylC$_2$alkyl, —C(O)—R$^9$, —C(O)-(alkyl)-O-(alkyl), alkoxycarbonyl, aryloxycarbonyl, benzyloxycarbonyl, —Si(R$^{10}$)(O$_{0-1}$R$^{11}$)$_2$, and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{1a}$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-C$_1$alkyl, heterocycloalkyl-C$_1$alkyl, alkoxycarbonylC$_2$alkyl, —C(O)—R$^9$, —C(O)-(alkyl)-O-(alkyl), alkoxycarbonyl, aryloxycarbonyl, benzyloxycarbonyl, —C(O)O—Si(R$^{17}$)$_3$, —Si(R$^{10}$)(O$_{0-1}$R$^{11}$)$_2$, —P(=O)(R$^{13}$)$_2$ and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{2a}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

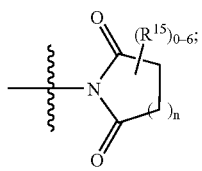

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C$(R^{14})_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

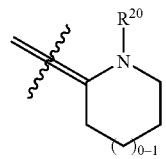

wherein $R^{20}$ is lower alkyl;

$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

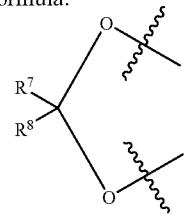

wherein $R^7$ and $R^8$ are same or different and are hydrogen, lower alkyl or are alkyl and are joined to form a cyclopentyl or cyclohexyl ring;

provided further that when $R^1$ is hydrogen, $R^2$ is other than methylcarbonyl or carboxyethyl;

or a pharmaceutically acceptable salt thereof.

30. A compound as in claim 29 of the formula (Ik)

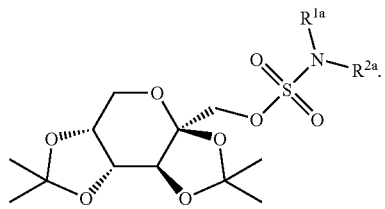

(Ik)

31. A product prepared by reacting a compound of formula (Ij)

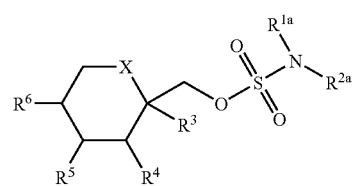

(Ij)

wherein

X is O;

$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —Si$(R^{10})(O_{0-1}R^{11})_2$, and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{1a}$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si($R^{17}$)$_3$, —Si($R^{10}$)(O$_{0-1}$ $R^{11}$)$_2$, —P(=O)($R^{13}$)$_2$ and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{2a}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl, aralkyl or heteroaryl; wherein the alkyl, aryl or heteroaryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

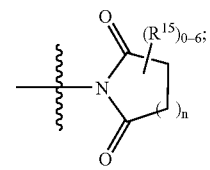

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C($R^{14}$)$_2$;

wherein each $R^{14}$ is independently selected from hydrogen, dialkylamino, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

alternatively, two $R^{14}$ groups are taken together with the carbon atom to which they are bound to form a heterocycloalkyl group of the formula

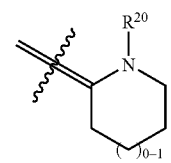

wherein $R^{20}$ is lower alkyl;

$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

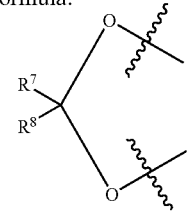

wherein $R^7$ and $R^8$ are same or different and are hydrogen, lower alkyl or are alkyl and are joined to form a cyclopentyl or cyclohexyl ring;

or a pharmaceutically acceptable salt thereof;

under de-protection conditions conditions, to yield a compound of formula (XX)

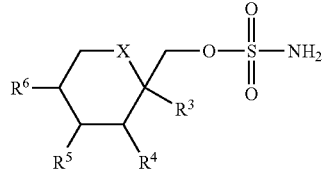

(XX)

wherein the radicals are defined above.

32. A product as in claim 31, wherein the compound of formula (Ij) is a compound of formula (Ik)

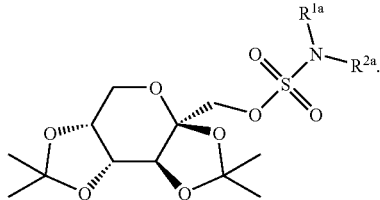

(Ik)

33. A compound of the formula (I)

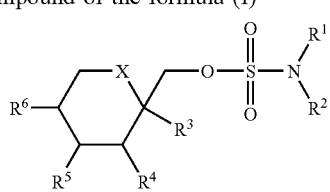

(I)

wherein
X is O;
R¹ is selected from the group consisting of hydrogen, alkyl, alkenyl, alkynyl, cycloalkyl, cycloalkyl-alkyl, cycloalkenyl, aryl, aralkyl, heteroaryl, heteroaryl-alkyl, heterocycloalkyl, heterocycloalkyl-alkyl, alkoxycarbonylalkyl, —($C_{2-8}$alkyl)-O—C(O)-(alkyl), —C(O)—$R^9$, —C(O)-(alkyl)-O-(alkyl), alkoxycarbonyl, aryloxycarbonyl, aralkyloxycarbonyl, —Si($R^{10}$)($O_{0-1}R^{11}$)$_2$, —SO$_2R^{12}$ and 2-(trimethylsilyl)ethoxymethyl;
wherein the alkyl, cycloalkyl, aryl, heteroaryl or heterocycloalkyl group, whether alone or as part of the R¹ substituent group, is optionally substituted with one or more substituents independently selected from halogen, hydroxy, carboxy, alkyl, alkoxy, aryl, aralkyl, amino, alkylamino, dialkylamino, nitro or cyano;
R² is selected from the group consisting of hydroxy, alkyl, alkoxy, alkenyl, alkynyl, cycloalkyl, cycloalkyl-alkyl, cycloalkenyl, aryl, aryloxy, aralkyl, aralkyloxy, heteroaryl, heteroaryl-alkyl, heterocycloalkyl, heterocycloalkylalkyl, alkoxycarbonylalkyl, —($C_{2-8}$alkyl)-O—C(O)-(alkyl), —C(O)—$R^9$, —C(O)-(alkyl)-O-(alkyl), alkoxycarbonyl, aryloxycarbonyl, aralkyloxycarbonyl, —C(O)O—Si($R^{17}$)$_3$, —Si($R^{10}$)($O_{0-1}R^{11}$)$_2$, —SO$_2R^{12}$, —P(=O)($R^{13}$)$_2$ and 2-(trimethylsilyl)ethoxymethyl;
wherein the alkyl, cycloalkyl, aryl, aralkyl, heteroaryl or heterocycloalkyl group, whether alone or as part of the R² substituent group, is optionally substituted with one or more substituents independently selected from halogen, hydroxy, carboxy, alkyl, alkoxy, aryl, aralkyl, amino, alkylamino, dialkylamino, nitro or cyano;
wherein each $R^9$ is independently selected from alkyl, aryl or aralkyl; wherein the alkyl or aryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;
wherein each $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;
wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;
wherein each $R^{12}$ is independently selected from alkyl, aryl, aralkyl or heteroaryl; wherein the alkyl, aryl or heteroaryl groups, whether alone or as part of an $R^{12}$ substituent group, is optionally substituted with one or more substituents independently selected from halogen, trifluoromethyl, trifluoromethoxy, alkyl, alkoxy, nitro, alkylcarbonylamino, arylcarbonylamino, aralkylcarbonylamino, aryl, benzenesulfonyl or phenoxy; wherein the phenoxy group is optionally substituted with one or more substituents independently selected from halogen, alkyl, alkoxy or nitro;
wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;
wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;
alternatively, R¹ and R² are taken together with the N atom to which they are bound to form a heteroaryl or heterocycloalkyl group; wherein the heteroaryl or heterocycloalkyl group is optionally substituted with one or more substituents independently selected from halogen, hydroxy, carboxy, oxo, alkyl, alkoxy, aryl, aralkyl, amino, alkylamino, dialkylamino, nitro, cyano, —C(=NH)-amino, —C(=NH)alkylamino or —C(=NH)-dialkylamino; wherein the aryl substituent is optionally substituted with one or more substituents independently selected from halogen, hydroxy, carboxy, alkyl, alkoxy, aryl, aralkyl, amino, alkylamino, dialkylamino, nitro, cyano, —C(=NH)-amino, —C(=NH)-alkylamino or —C(=NH)-dialkylamino; wherein the —C(=NH)-amino, —C(=NH)-alkylamino or —C(=NH)-dialkylamino group is bound to a nitrogen or carbon atom on the aryl, heteroaryl or heterocycloalkyl; and wherein no more than one —C(=NH)-amino, —C(=NH)-alkylamino or —C(=NH)-dialkylamino group is bound to the aryl, heteroaryl or heterocycloalkyl;

alternatively $R^1$ and $R^2$ are taken together with the nitrogen atom to which they are bound to form —N═C$(R^{14})_2$;

wherein each $R^{14}$ is independently selected from hydrogen, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano; provided that at least one $R^{14}$ is selected from the group consisting of hydrogen and alkyl;

$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

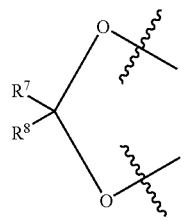

wherein $R^7$ and $R^8$ are the same or different and are hydrogen, lower alkyl or are alkyl and are joined to form a cyclopentyl or cyclohexyl ring;

provided that when $R^1$ is alkyl, $R^2$ is other than alkyl;

provided further that when $R^1$ is hydrogen, $R^2$ is other than alkyl, methylcarbonyl, phenyl, benzyl or carboxyalkyl;

provided further that $R^1$ and $R^2$ when taken together with the nitrogen atom to which they are bound is other than imidazolyl;

provided further that when X is O, $R^3$ and $R^4$ are taken together to form a methylenedioxy group of the formula:

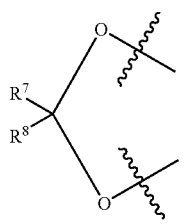

$R^5$ and $R^6$ are taken together to form a methylenedioxy group of the formula:

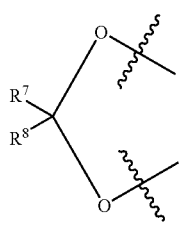

wherein $R^7$ and $R^8$ in each instance are each methyl, and $R^1$ is hydrogen then $R^2$ is other than isopropylsulfonyl, 4-(N-benzyl)-piperidinyl or 4-pyridyl;

or a pharmaceutically acceptable salt thereof.

34. A process for the preparation of a compound of formula (XX)

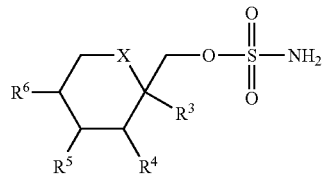

wherein
X is O;
$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

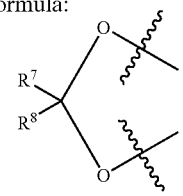

wherein $R^7$ and $R^8$ are same or different and are hydrogen, lower alkyl or are alkyl and are joined to form a cyclopentyl or cyclohexyl ring;

or a pharmaceutically acceptable salt thereof;

comprising, reacting a compound of formula (Ij)

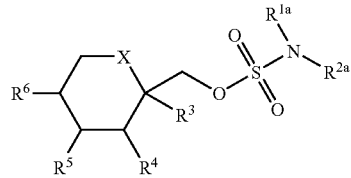

wherein
X is O;
$R^{1a}$ is selected from the group consisting of hydrogen, substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), heteroaryl-$C_1$alkyl, heterocycloalkyl-$C_1$alkyl, alkoxycarbonylc$_2$alkyl, —C(O)—$R^9$, —C(O)-(alkyl)-O-(alkyl), alkoxycarbonyl, aryloxycarbonyl, benzyloxycarbonyl, —Si($R^{10}$)(O$_{0-1}$$R^{11}$)$_2$, and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{1a}$ substituent group, is optionally substituted with one or more substituents independently selected from halogen, hydroxy, carboxy, alkyl, alkoxy, aryl, aralkyl, amino, alkylamino, dialkylamino, nitro or cyano;

$R^{2a}$ is selected from the group consisting of substituted ethyl, alkenyl (wherein the double bond of the alkenyl group is directly bound to or one carbon atom removed from the nitrogen), cycloalkenyl (wherein the double bond of the cycloalkenyl group is directly bound to or one carbon atom removed from the nitrogen), benzyloxy, heteroaryl-$C_1$alkyl, heterocycloalkyl-$C_1$alkyl, alkoxycarbonyl$C_2$alkyl, —C(O)—$R^9$, —C(O)-(alkyl)-O-(alkyl), alkoxycarbonyl, aryloxycarbonyl, benzyloxycarbonyl, —C(O)O—Si($R^{17}$)$_3$, —Si($R^{10}$)($O_{0-1}R^{11}$)$_2$, —P(=O)($R^{13}$)$_2$ and 2-(trimethylsilyl)ethoxymethyl;

wherein the substituents on the ethyl group are one or more substituents independently selected from halogen, carboxy, amino, alkylamino, dialkylamino, nitro or cyano;

wherein the alkyl, benzyl, heteroaryl or heterocycloalkyl group, whether alone or as part of the $R^{2a}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^9$ is independently selected from alkyl, aryl or aralkyl; wherein the alkyl or aryl group, whether alone or as part of an $R^9$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein $R^{10}$ is independently selected from hydrogen, alkyl, aryl or aralkyl; wherein the alkyl or aryl group, whether alone or as part of an $R^{10}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{11}$ is independently selected from alkyl, aryl or aralkyl; wherein the alkyl or aryl group, whether alone or as part of an $R^{11}$ substituent group, is optionally substituted with one or more substituents independently selected from halogen, hydroxy, carboxy, alkyl, alkoxy, alkoxycarbonyl, aryl, aralkyl, amino, alkylamino, dialkylamino, nitro or cyano;

wherein each $R^{13}$ is independently selected from alkyl, alkoxy, aryl, aryloxy, aralkyl or aralkyloxy; wherein the alkyl or aryl group, whether alone or as part of an $R^{13}$ substituent group, is optionally substituted with one or more substituents independently selected from halogen, hydroxy, carboxy, alkyl, alkoxy, aryl, aralkyl, amino, alkylamino, dialkylamino, nitro or cyano;

wherein each $R^{17}$ is independently selected from alkyl, aryl or aralkyl; wherein the alkyl or aryl group, whether alone or as part of an $R^{17}$ substituent group, is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form a group of the formula

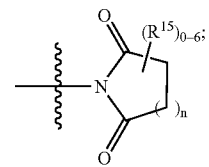

wherein n is an integer from 1 to 3; and wherein each $R^{15}$ is independently selected from the group consisting of halogen, hydroxy, carboxy, alkyl, alkoxy, aryl, aralkyl, amino, alkylamino, dialkylamino, nitro and cyano;

alternatively two $R^{15}$ groups are taken together with the carbon atoms to which they are bound to form a phenyl ring; wherein the phenyl ring is optionally substituted with one or more substituents independently selected from halogen, hydroxy, carboxy, alkyl, alkoxy, aryl, aralkyl, amino, alkylamino, dialkylamino, nitro or cyano;

alternatively $R^{1a}$ and $R^{2a}$ are taken together with the nitrogen atom to which they are bound to form —N=C($R^{14}$)$_2$;

wherein each $R^{14}$ is independently selected from hydrogen, alkyl, cycloalkyl, aryl or aralkyl; wherein the alkyl, cycloalkyl or aryl group, whether alone or as part of an $R^{14}$ substituent group, is optionally substituted with one or more substituents independently selected from halogen, hydroxy, carboxy, alkyl, alkoxy, aryl, aralkyl, amino, alkylamino, dialkylamino, nitro or cyano;

provided that at least one $R^{14}$ is selected from the group consisting of hydrogen and alkyl;

$R^3$, $R^4$, $R^5$ and $R^6$ are each independently selected from hydrogen or lower alkyl and, when X is O, $R^3$ and $R^4$ and/or $R^5$ and $R^6$ together may be a methylenedioxy group of the formula:

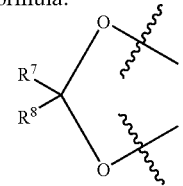

wherein $R^7$ and $R^8$ are same or different and are hydrogen, lower alkyl or are alkyl and are joined to form a cyclopentyl or cyclohexyl ring;

or a pharmaceutically acceptable salt thereof;

under de-protection conditions, to yield the corresponding compound of formula (XX).

* * * * *